United States Patent
Wolf et al.

(10) Patent No.: US 12,311,165 B2
(45) Date of Patent: May 27, 2025

(54) IMPLANTABLE ENDOVASCULAR, LOW PROFILE INTRACARDIAC LEFT ATRIAL RESTRAINING DEVICES FOR LOW ENERGY ATRIAL CARDIOVERSION, PACING AND SENSING

(71) Applicant: Randall K. Wolf, Houston, TX (US)

(72) Inventors: Randall K. Wolf, Houston, TX (US); Paul Spence, Aventura, FL (US)

(73) Assignee: Wolf Cardio, LLC, Houston, TX (US)

( * ) Notice: Subject to any disclaimer, the term of this patent is extended or adjusted under 35 U.S.C. 154(b) by 0 days.

(21) Appl. No.: 18/679,350

(22) Filed: May 30, 2024

(65) Prior Publication Data

US 2024/0316341 A1    Sep. 26, 2024

Related U.S. Application Data

(63) Continuation of application No. 17/782,578, filed as application No. PCT/US2020/063664 on Dec. 7, 2020.

(Continued)

(51) Int. Cl.
*A61N 1/00*  (2006.01)
*A61N 1/05*  (2006.01)
*A61N 1/362*  (2006.01)

(52) U.S. Cl.
CPC ........... *A61N 1/0563* (2013.01); *A61N 1/057* (2013.01); *A61N 1/3624* (2013.01)

(58) Field of Classification Search
None
See application file for complete search history.

(56) References Cited

U.S. PATENT DOCUMENTS 5,755,761 A    5/1998  Obino
5,855,592 A    1/1999  McGee et al.
(Continued)

FOREIGN PATENT DOCUMENTS

WO    WO-9510226 A1 *  4/1995  ......... A61B 18/1492
WO    WO-2018/085545 A1  5/2018
(Continued)

OTHER PUBLICATIONS

Extended European Search Report for EP Pat. App. No. 20896265.4 dated Nov. 15, 2023, 9 pgs.
(Continued)

*Primary Examiner* — Gary Jackson
*Assistant Examiner* — Anant A Gupta
(74) *Attorney, Agent, or Firm* — Foley & Lardner LLP

(57) ABSTRACT

Disclosed are various configurations of electrodes with accompanying extensions and wires configured to be attached at or near the left atrium of a heart to allow the device to be held snug against the endocardium and out of the blood flow for low energy defibrillation of the atria in response to atrial fibrillation or other atrial arrhythmias. The portion of the lead internal to the atrium (e.g., the left atrium) is restrained against the endocardium of the left atrium by way of a restraint mechanism. In one example, the electrode is configured to attach to the atrial septum, with wires containing memory-shaped metal to keep the wires against the heart wall. In yet another example, the electrode is configured to be part of a mitral valve device.

30 Claims, 21 Drawing Sheets

Related U.S. Application Data

(60) Provisional application No. 62/944,540, filed on Dec. 6, 2019.

(56) References Cited

U.S. PATENT DOCUMENTS

| | | | |
|---|---|---|---|
| 6,516,231 B1 | 2/2003 | Flammang | |
| 7,448,999 B1* | 11/2008 | Karicherla | A61B 5/6858 600/486 |
| 7,515,971 B1* | 4/2009 | Doan | A61B 5/0215 600/375 |
| 8,021,359 B2 | 9/2011 | Auth et al. | |
| 8,543,193 B2 | 9/2013 | Satin et al. | |
| 8,849,384 B2 | 9/2014 | Greenspan | |
| 9,492,657 B2* | 11/2016 | Gerber | A61N 1/0558 |
| 2005/0119647 A1 | 6/2005 | He et al. | |
| 2006/0041300 A1 | 2/2006 | Zhang et al. | |
| 2007/0073179 A1 | 3/2007 | Afonso et al. | |
| 2009/0198297 A1 | 8/2009 | Zhang et al. | |
| 2010/0317981 A1 | 12/2010 | Grunwald | |
| 2012/0172944 A1 | 7/2012 | Dori et al. | |
| 2013/0331920 A1* | 12/2013 | Osypka | A61N 1/0587 607/122 |
| 2014/0207202 A1 | 7/2014 | Imran | |
| 2016/0325079 A1 | 11/2016 | Osypka | |
| 2016/0354600 A1 | 12/2016 | Kolberg et al. | |
| 2017/0281031 A1 | 10/2017 | Houben et al. | |
| 2018/0296842 A1 | 10/2018 | Imran | |
| 2020/0054882 A1 | 2/2020 | Dale et al. | |
| 2021/0369394 A1 | 12/2021 | Braido et al. | |
| 2023/0264017 A1 | 8/2023 | Wolf et al. | |

FOREIGN PATENT DOCUMENTS

| | | |
|---|---|---|
| WO | WO-2021/113843 A1 | 6/2021 |
| WO | WO-2022/076801 A1 | 4/2022 |

OTHER PUBLICATIONS

International Search Report and Written Opinion on PCT/US2023/063074 dated Oct. 10, 2023, 13 pgs.

International Search Report on PCT/US2020/63664 Dtd Mar. 10, 2021, 3 pgs.

International Search Report and Written Opinion for PCT/US2024/016776 dated Aug. 8, 2024, 13 pages.

* cited by examiner

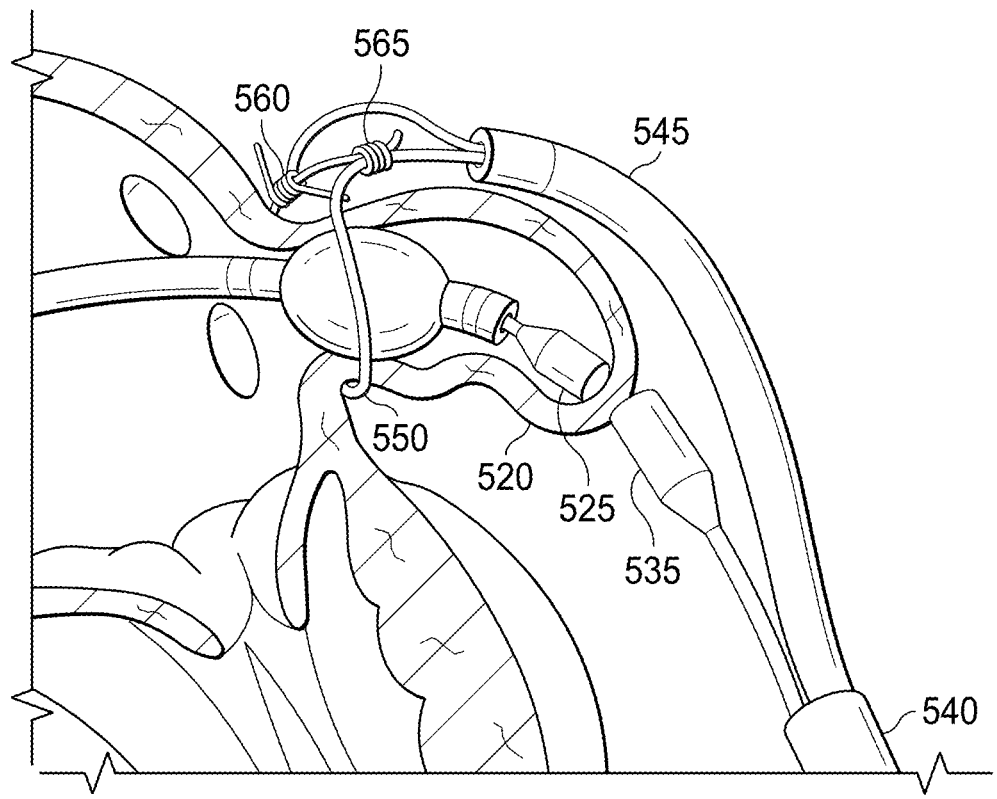
FIG. 6C
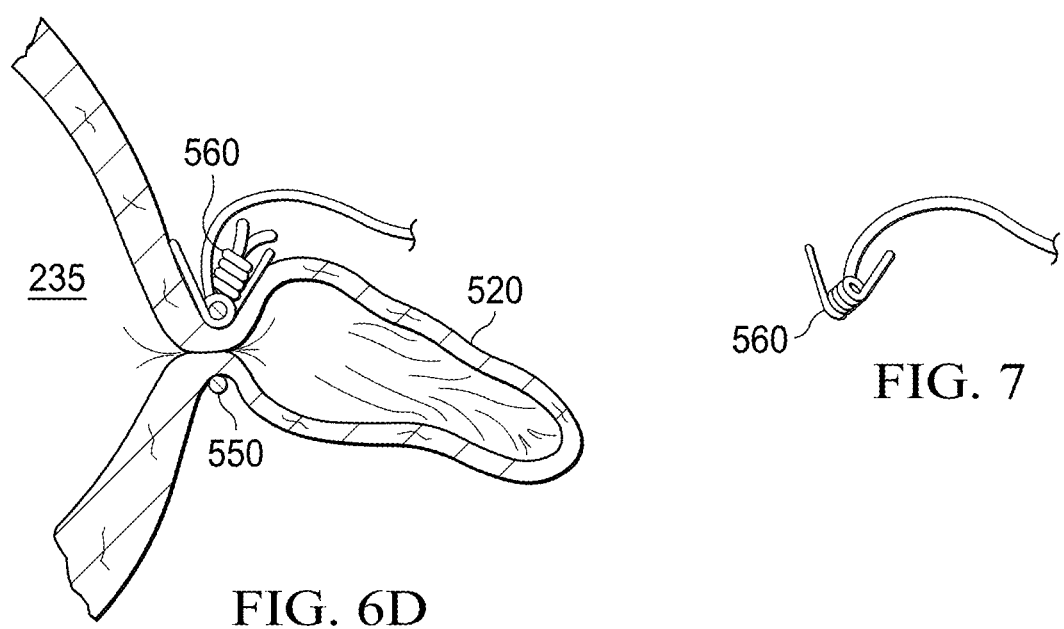
FIG. 6D
FIG. 7

IMPLANTABLE ENDOVASCULAR, LOW PROFILE INTRACARDIAC LEFT ATRIAL RESTRAINING DEVICES FOR LOW ENERGY ATRIAL CARDIOVERSION, PACING AND SENSING

CROSS-REFERENCE TO RELATED APPLICATIONS

This application is a continuation of U.S. patent application Ser. No. 17/782,578, filed Dec. 7, 2020, and titled "IMPLANTABLE ENDOVASCULAR, LOW PROFILE INTRACARDIAC LEFT ATRIAL RESTRAINING DEVICES FOR LOW ENERGY ATRIAL CARDIOVERSION, PACING AND SENSING", which is a PCT National Phase of PCT/US2020/063664, filed, Dec. 7, 2020, and titled "IMPLANTABLE ENDOVASCULAR, LOW PROFILE INTRACARDIAC LEFT ATRIAL RESTRAINING DEVICES FOR LOW ENERGY ATRIAL CARDIOVERSION, PACING AND SENSING", which is a Paris Convention of U.S. Provisional Patent Application Ser. No. 62/944,540, filed Dec. 6, 2019, and titled "IMPLANTABLE ENDOVASCULAR, LOW PROFILE INTRACARDIAC LEFT ATRIAL RESTRAINING DEVICES FOR ULTRA LOW ENERGY ATRIAL CARDIOVERSION", the disclosures of which are incorporated herein by reference in their entirety.

BACKGROUND

Wires placed in the heart connected to pacemakers have been used in the right side of the human heart since 1957 (Earl Bakken-founder of Medtronic). Since then millions of wires for sensing, pacing and defibrillating the heart have extended and saved lives around the world. Despite this body of work, wires are not used on the left side of the heart. Mitral valve devices, left atrial occlusion devices, and septal occlusion devices have been placed on the left side of the heart for decades. However, wires traditionally have not been placed on the left side of the heart because of the risk that a thrombus collecting on a wire floating free in the heart can detach. If the wire is on the right side of the heart, and a thrombus develops and detaches, the thrombus can only travel to the lungs, and intrinsic enzymes can be used to break down the dot. However, if a wire is on the left side of the heart and a thrombus develops and detaches, the dot will travel into the aorta and to the brain. The brain has no intrinsic mechanism to dissolve the dot, and a stroke can occur, which can be devastating.

Defibrillating the human heart has saved many lives. Initially performed only externally (through the skin), defibrillators are now placed internally (endovascular and intracardiac and extracardiac) to emergently defibrillate the heart to terminate dangerous arrhythmias. Current defibrillators need relatively high energy (as measured in joules) to defibrillate the heart. These shocks are painful to the patient and cause incredible anxiety. The energy utilized wears down the batteries quickly, which then require replacing. Replacing the generators and batteries are expensive (the batteries are incorporated into the generators) and there is the risk of infection with generator and battery replacement. Infections are sometimes fatal and are very expensive to the medical system.

Atrial fibrillation (AF), the most common human cardiac arrhythmia, causes great morbidity, mortality and cost. Although AF is present only in the atrial chambers of the heart today the entire heart is defibrillated for AF because leads to the heart for defibrillation generally do not include leads placed in the left atrium (LA). Accordingly, it is difficult to sense the LA for the occurrence of arrhythmias and difficult to selectively defibrillate the LA. As such, defibrillating the heart in response to AF generally requires defibrillating the entire heart.

SUMMARY

The embodiments described herein pertain to various configurations of low profile electrodes and accompanying structures that hold the electrodes and wires against the endocardium (eliminating free floating wires) and configured to be attached at or near the left atrium of the heart to allow for low energy recording, sensing, pacing, and/or defibrillation of the atria in response to atrial fibrillation or other atrial arrhythmias. In addition to defibrillating the upper chambers of the heart, these electrodes and accompanying structures can be utilized to sense and map normal and abnormal electrical impulses. The devices can also be used in conjunction with leads implanted in the right atrium, the right ventricle, the coronary sinus and leads on the outside of the heart. In one embodiment, the electrode is configured to attach to the atrial septum, with the wire attachment that holds the wires against the heart tissue. In another embodiment, the electrode configuration is attached to a modified atrial septal closure device (could also be an atrial septal opening device, again with the special attachment keeping the wires held fast against the heart wall. In another embodiment, the electrode is configured to be part of an atrial appendage closure device, also with the special attachment that keeps the wire from free floating, on either the inside (endocardial surface) or outside (epicardial surface) of the heart In yet another embodiment the electrode is configured to be part of a mitral valve device, or may be incorporated into any valve repair or replacement device, whether placed by conventional open heart surgery or by an endovascular technique.

A beneficial feature is that these embodiments allow the electrodes and wires to be held fast against the heart tissue, which like mitral devices commercially available, avoid thrombus formation on the electrodes and wires. The described devices then allow sensing, pacing and/or defibrillation of the left side of the heart that has not been clinically addressed before. For instance, these devices could be used to directly pace the left atrium. Traditionally, only the right atrium can be accessed for pacing. In many patients, because of intrinsic conduction issues or distension of the atria, the right atrial pacing is not always in synch with the left atrium. With the new device in the intratribal septum, the left atrium or about the left atrium-in clinical practice both atria can be paced. This could allow for synchronous bi-atrial pacing, which improves the efficacy of atrial pacing and would improve cardiac output and ejection fraction in some patients.

BRIEF DESCRIPTION OF THE DRAWINGS

For a detailed description of various examples, reference will now be made to the accompanying drawings in which:

FIGS. 6A-6D illustrate a medical procedure for implanting the closure device and associated electrode of FIG. 5.

FIG. 7 shows a dose-up view of one example of the electrode configured to be coupled to the atrial appendage closure device of FIG. 5.

DETAILED DESCRIPTION

Figure 1:
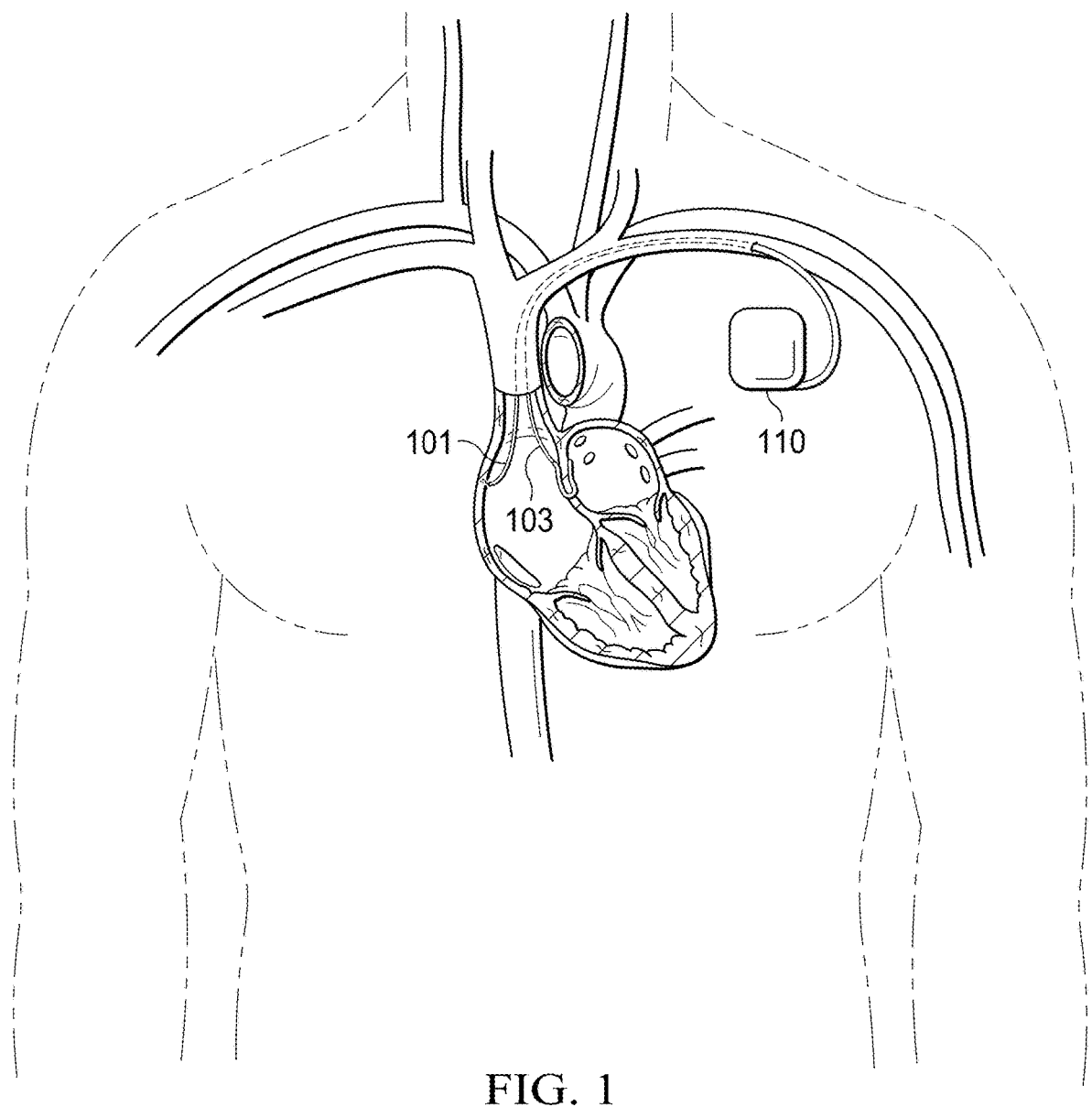
FIG. 1 illustrates a septal electrode attached to the atrial septum, and its extensions which keep the wires against the heart tissue.

Low profile restraining devices are described herein which eliminate the problem of current intracardiac leads which generally are permitted to free float within the interior volume of the corresponding cardiac chamber. The described embodiments include a mechanism that keep a portion of the lead fixed against the endocardium of the left atrium, where the electrode and lead will become embedded against the wall of the heart. Thus, thrombus is avoided with the described low-profile devices on the left side of the heart. Placement of the leads, with these devices, on the left side of the heart facilitates new therapies for the treatment of cardiac disease. The restraint mechanisms described herein can be extended to other chambers of the heart.

Beneficially, the described examples are directed to leads connected to the left atrium. For atrial arrhythmias (arrhythmias in the upper chambers of the heart), left atrial leads is a better way to sense AF and selectively defibrillate the upper chambers. A much lower energy can be used (1-10 joules) compared to defibrillating the entire heart. Accordingly, the patient experiences much less discomfort and battery life is increased. Leads in the LA can also provide a record of where the AF is initiating, which could guide further treatment to eliminate the focus. A left atrial lead requires careful design to avoid thrombus and embolism. The embodiments described herein pertain to a device placed entirely by a minimally invasive route. The device is low profile and sits flat against the endocardial wall and becomes strongly embedded in tissue. The low nature of the device avoids or reduces the risk of thrombus formation. The described device provides a solution for sensing and treating AF and other supraventricular arrhythmias, with lower power, and with shocks that are less painful to the patient. The embodiments described herein pertain to an implantable device that is connected to wires that contain nitinol or other types of shape memory metal that creates some torsion that keeps the wires against the walls of the heart and prevents free floating wires. These devices can be placed in or around the left atrium of the heart, as well as on the right side of the heart. The restraining device applies passive force to the tissue by a curved wire bent to a looped state to provide a suitable amount of torsion. The devices can have protrusions to hold the device in place and prevent slippage until tissue healing occurs. The electrode portion of the device can be coated with materials such as gold to increase its conductivity. Incorporated into the curved wire is an extension of conducting wire, also coated with a material to improve conduction (such as gold plating), to increase the surface area of the device. Beneficially, the extension will lie against the heart tissue, because of wire torsion. The device is also incorporated with insulated wire(s) that will hug the heart wall. The insulated portion of the device will have an outer nitinol or other shape metal that keeps the wires out of the blood stream. As in other devices in the heart that abut the endocardial surface, this device and its extensions and will become incorporated into the atrial tissue and will remain out of the flow of blood through the heart.

The devices then exit the heart, as with commercially available devices, to connect to a pacemaker, defibrillator or transducer or some combination of the these. This allows the device to receive and transmit an electrical charge from a remote site, such as a transducer or pacemaker. The transducer and pacemaker devices are available from several manufacturers, such as Medtronic and St Jude Medical. The device sits flat against the atrial septal wall and becomes strongly embedded in tissue. This low profile discourages thrombus formation, and therefore allows the devices to be placed on the left side of the heart. In clinical practice, the devices with the extensions can be used on the right side of the heart also. The device has excellent electrical contact The restraining device is held passively against the atrial septum. The unique property of the restraining device easily attaching to the atrial septum with a low profile provides a safe route for deployment. Since the extensions and the wires are constructed with a shaped memory metal or other material that holds the extensions and wires against the endocardium, the device can be deployed on the left side of the heart Currently transseptal punctures are commonplace during electrophysiologic (EP) studies. The wires for deployment of the device, such as a transseptal sheath and guidewire and obturator are already ideally situated during the transseptal puncture, which is utilized to enter the left atrium. Usually these EP studies are for the treatment of AF, so it would be straight-forward to place the restraining device during an EP procedure. Prior ways to achieve good electrical contact inside the heart include screws, barbs, hooks, pins and electrode plates. All these can be incorporated into the distal restraining device and to the extensions and special wires to help hold the devices against the heart wall. This also ensures good electrical contact. The device can incorporate coatings such as steroids to prevent fibrosis, low contact or high energy. The device can include a bioabsorbable component, such that after the electrode becomes embedded in tissue, the remaining restraining portion of the device reabsorbs. The device may also contain an antithrombotic coating, which helps prevent thrombus formation until the device is surrounded by tissue ingrowth. The device is carefully designed to be low profile, but with enough strength in the deployed position to provide complete stability in the intra-atrial septum.

The restraining device can be integrated into any other device placed in or around the left or right atrium. The restraining device can be modified to work with any device that is to be placed in or around the right or left atrium, including, but not limited to atrial septal closure devices, left atrial closure devices (both intra and extracardiac) and valve repair or replacement devices. In the case of a septal occlusion device, the restraining device is modified to be incorporated into the rings of the septal closure device. Several possible iterations include three electrode conducting rings around the areas of the septal device that abut the endocardium of the septum. The exact configuration of the wire array can be changed depending on the device configuration, the surface area in contact, and the resistance generated. In the case of a mitral valve replacement, the retraining device can be modified to fit in a groove where the valve device abuts atrial tissue. The wire electrodes of the device may be circular or may be cross-hatched, or other configuration to provide the therapeutically sufficient electrical output at the lowest energy with a suitable resistance profile.

The retraining device could be delivered together with the valve or separately. The distal end of the lead can be affixed to, for example, the atrial septum, in or around the left atrial appendage, or in a mitral valve device. This allows for low energy defibrillation of the atria in response to atrial fibrillation or other atrial arrhythmias. The device can also be used to sense electrical activity on the endocardial surface. It can be used in conjunction with other leads and wires in both atria of the heart, or left atria and either right ventricle, left ventricle or coronary sinus that can be used to defibrillate the atria. It can be used in conjunction with electrodes on the outside of the heart as well, such as epicardial leads and electrodes. A lead placed inside the atria can facilitate defibrillation using a relatively low energy (1-10 Joules, J) waveform to reliably defibrillate or pace the atria.

The lead and accompanying extensions and wires can be placed into the patient via blood vessels in the groin or neck area. The distal region of the lead has electrodes and is placed in or around the left atrium (e.g., atrial septum, in or around the left atrial appendage, or in a mitral valve device). The wire configuration keeps the wires against the heart walls. The proximal end of the wire can be connected to a small defibrillator unit or a transducer that is placed subcutaneously in the patient. Such pacemakers and defibrillators can sense, pace and defibrillate. Because of the novel placement of the device, the upper chambers of the heart, the atria, can be selectively defibrillated, allowing for a very low energy defibrillation. The device also allows for sensing directly in the left atrium, which could be used to detect the origin of arrhythmias and could be used to selectively pace the left atrium. If a transducer is used, power can be transferred to the transducer transcutaneously from an external device.

In one embodiment and as noted above, a restraining device is used to hold the left atrial wire in place against the atrial septum. A restraining device is a passive mechanical device that allows atrial defibrillation of both atria. Two devices are illustrated in FIGS. 1-4B. One is a device that has a spring effect to provide adequate restraining force to hold the wire in place against the septum, but without damaging the septum. This device can have protrusions to help hold the device in place and prevent slippage until healing occurs. This device can have extensions to provide for additional surface area for optimal sensing, pacing, and defibrillation. The extensions contain memory shaped metal or other similar substance to provide torsion, which keeps the extensions against the walls of the heart and out of the flow of blood through the heart. The second device is an array that attaches to or replaces an atrial septal defect closure device. Both can be placed in the patient at the end of a medical procedure such as a catheter ablation procedure to treat atrial fibrillation, or as a stand-alone procedure. Through a combined groin and subclavian approach (the left subclavian approach is illustrated), the wires placed from the groin can be brought to the subcutaneous position in the subclavian area, and then the defibrillator device can be placed.

FIG. 1 depicts an arrangement of the leads with one cardiac atrial lead 101 placed in the right atrium (similar to the atrial lead of a dual chamber pacing configuration). Part of this embodiment is the placement of a second cardiac atrial lead 103 (the device) in the left atrium, which allows for specific atrial sensing, pacing, and/or defibrillation, with a very small amount of energy (approximately 1-10 joules). The distal end of the left atrial lead 103 includes a shape memory structure that is configured to hold a portion of the lead 103 against a person's endocardium. The shape memory structure in this example is configured to be restrained to opposites sides of the atrial septum.

FIG. 1 also shows an electronics enclosure 110 which comprises a sealed enclosure containing a battery and a circuit. In one example, the circuit can generate the stimulation energy to electrodes at the distal region of the lead(s) 101, 103 for pacing and/or for defibrillation. The circuit additionally or alternatively can sense and record the electrical activity from the electrode(s). The electronics enclosure device 110 may be a pacemaker, a defibrillator, a device that both paces and defibrillates, and/or a sensing or recording device.

Figure 2A:
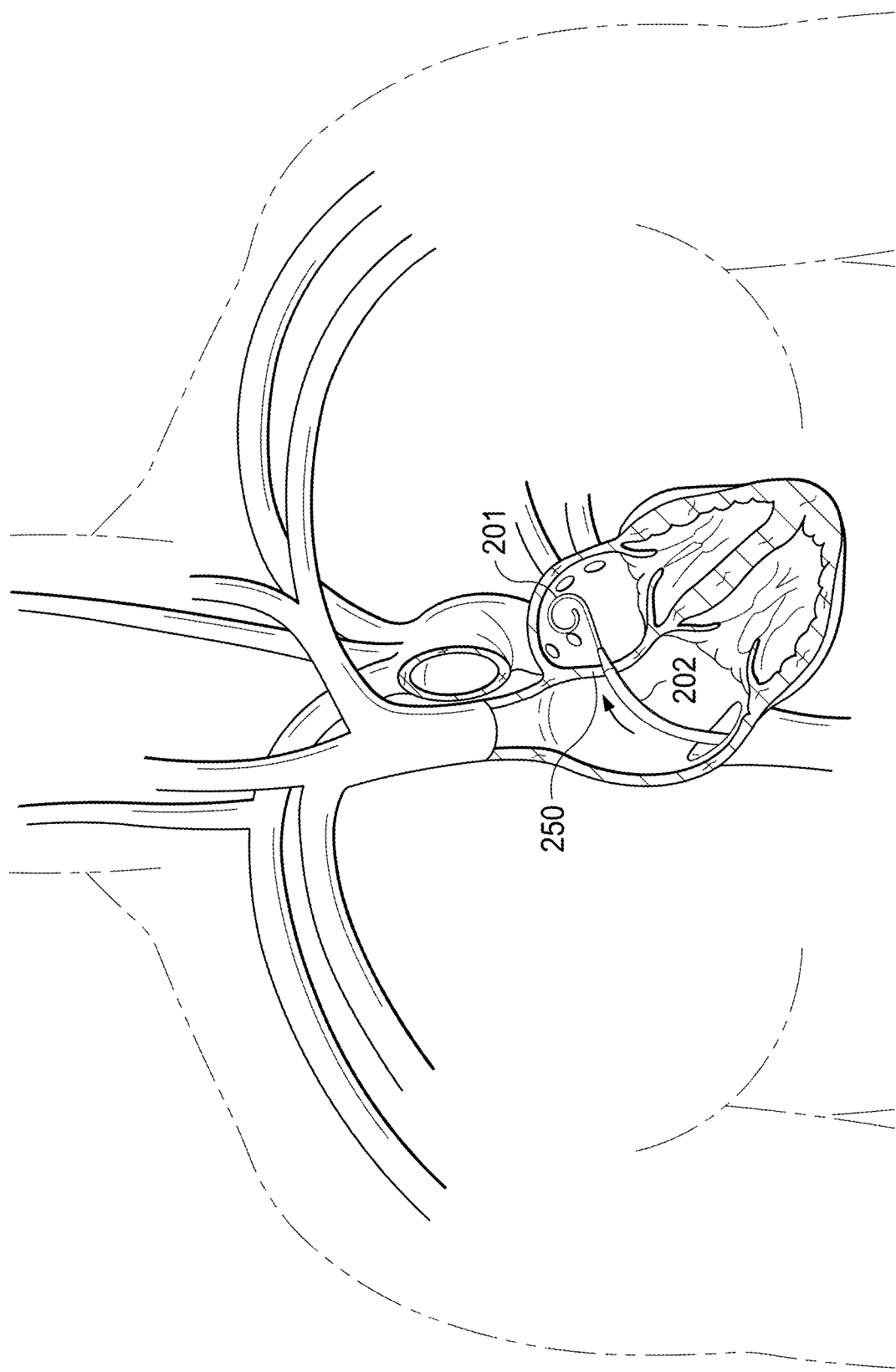
FIGS. 2A-2H illustrate a sequence of steps to attach the septal electrode during a surgical procedure.
Figure 2B:
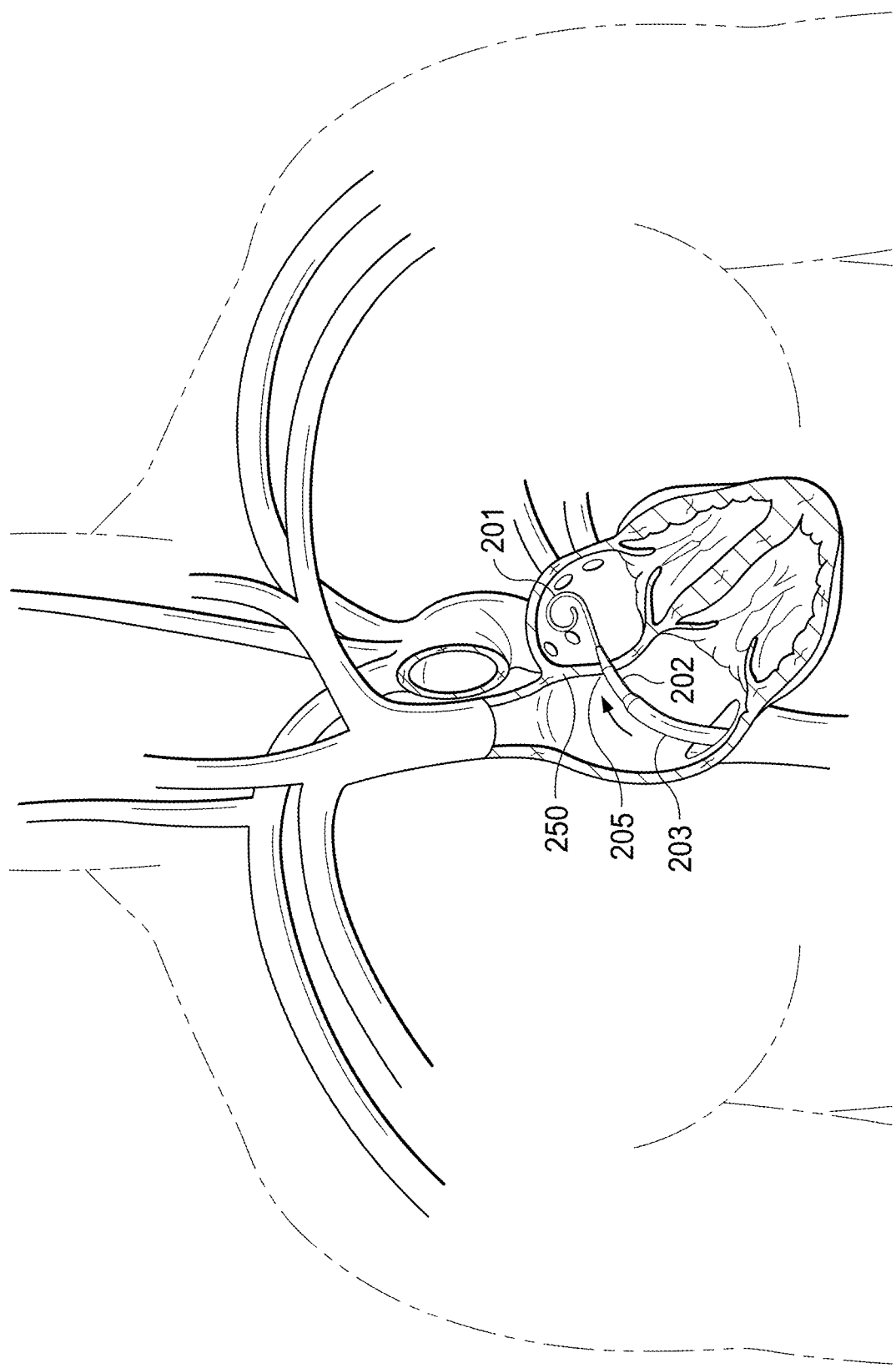
Figure 2C:
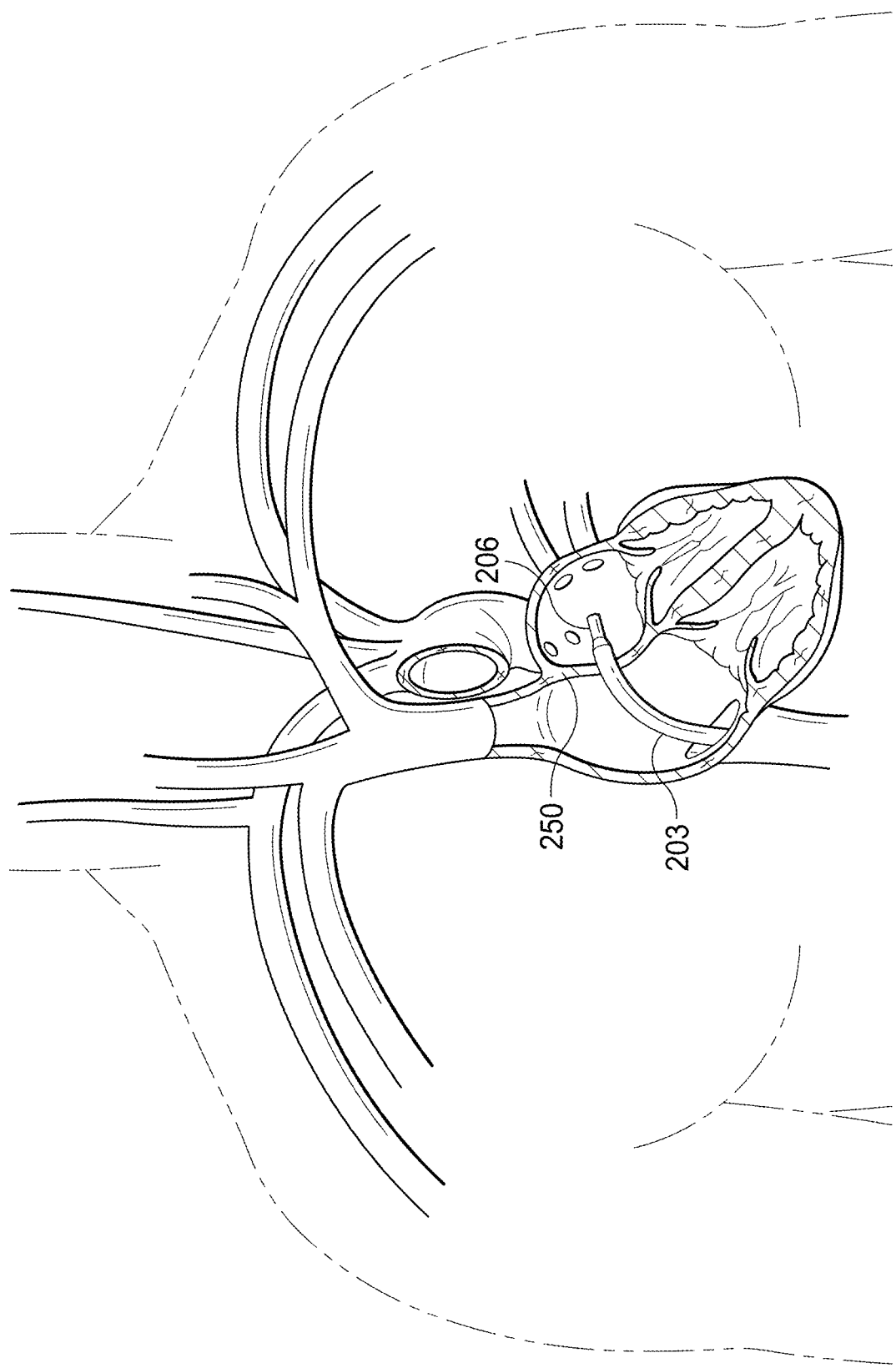
Figure 2D:
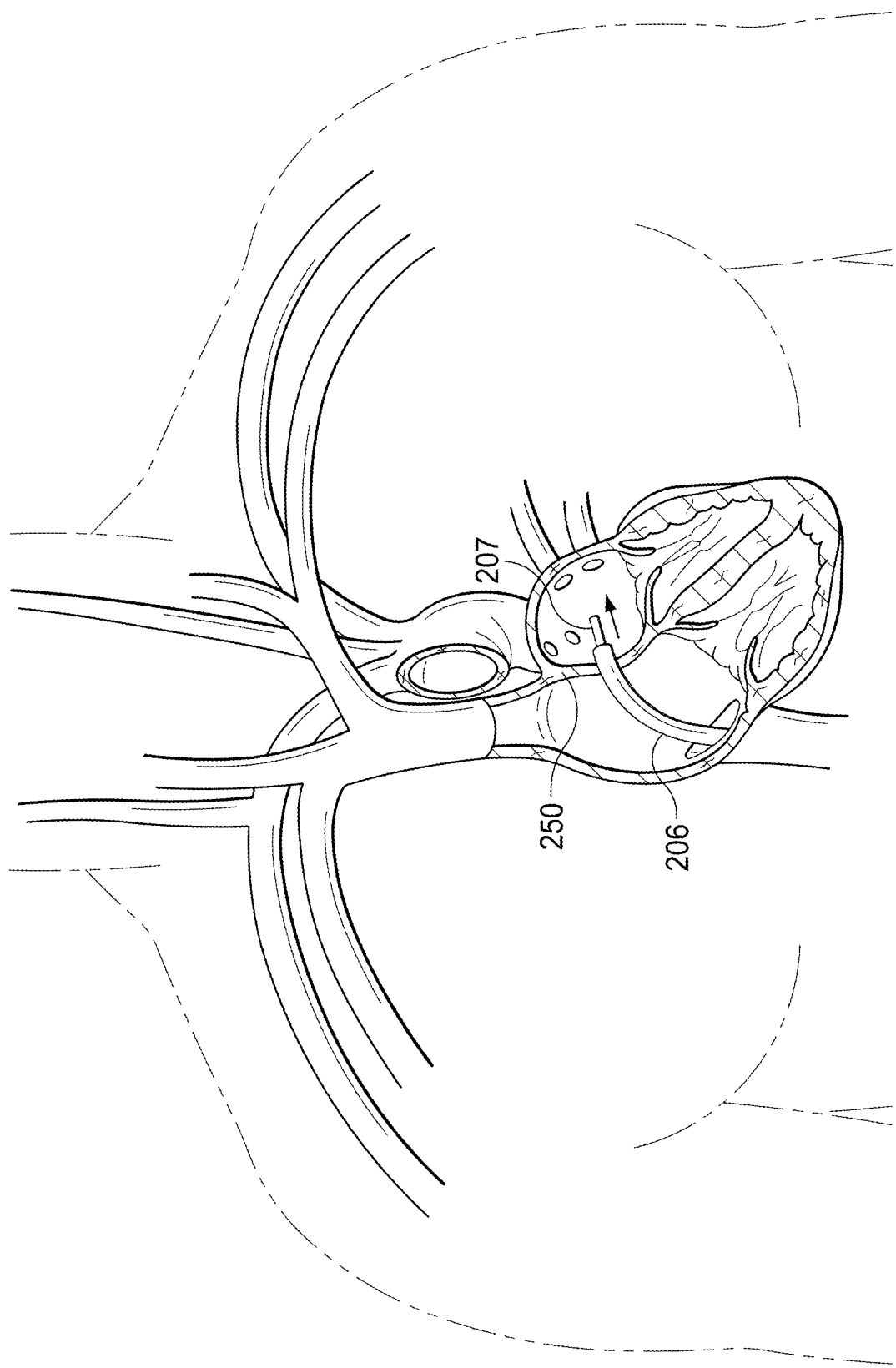
Figure 2E:
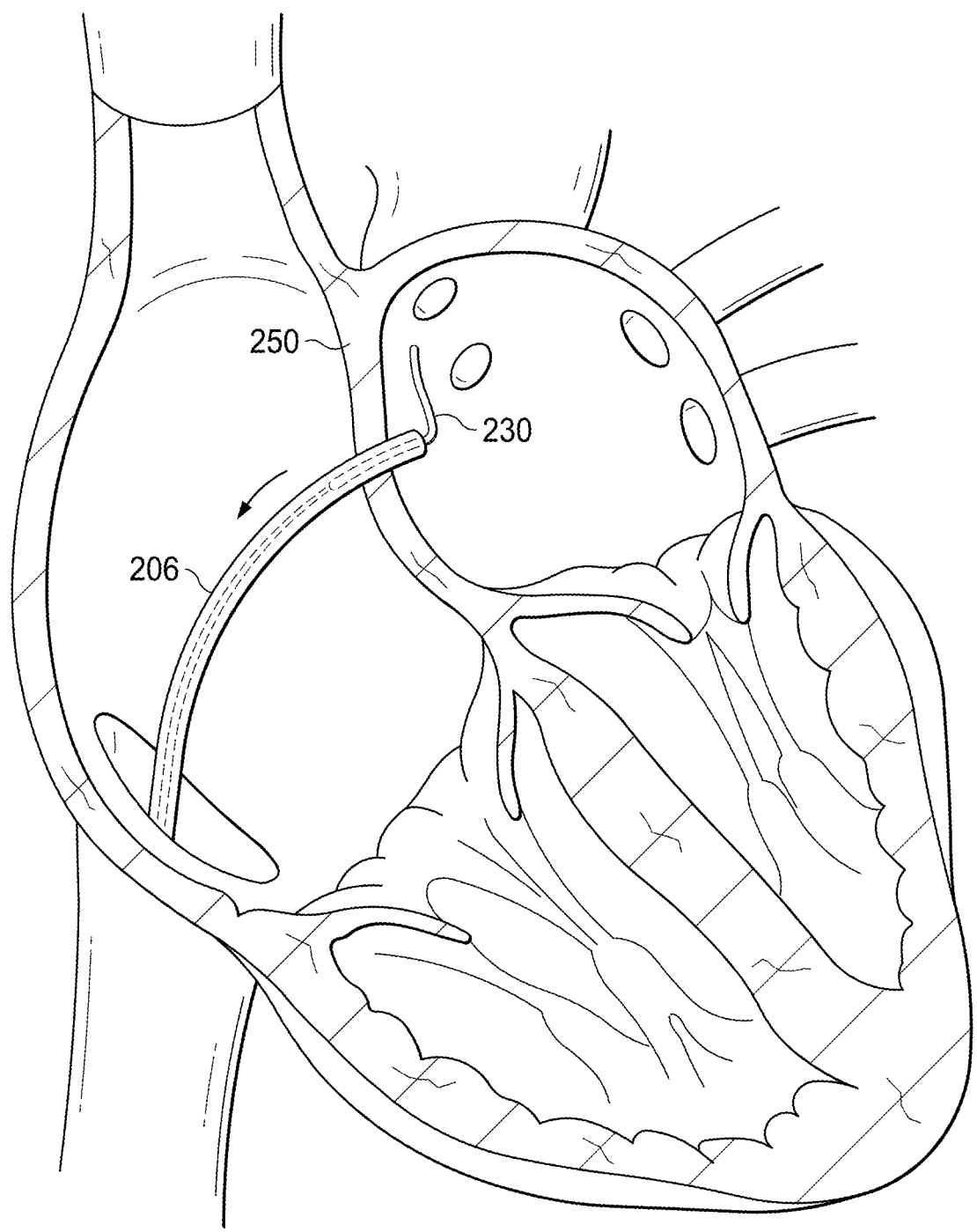

FIGS. 2A-2H illustrate a step-by-step procedure for attaching the leads to the heart. FIG. 2A depicts the initial transseptal puncture with a modified Seldinger technique. A guidewire 201 has been inserted via, for example, the groin and, through an obturator 202, into the left atrium. FIG. 2B depicts placing a transseptal sheath 203 through the transseptal puncture site 205 of the atrial septum 250. FIG. 2C depicts that the obturator 202 has been removed, and the transseptal sheath 203 remains in place with initial delivery of an anchor delivery sheath 206. The guidewire 201 has been removed. FIG. 2D depicts a septal electrode 230 (carrier or assembly) at the end of lead 103 exposed in the left atrium. The obturator 202 has been removed. FIG. 2E depicts the anchor delivery sheath 206 being retracted thereby exposing the septal electrode 230. The septal electrode 230 comprises a flexible elongate electrode. As can be seen, the distal region of the septal electrode 230 has a natural angled bend (approximately a right-angle bend) to it as shown.

Figure 2F:
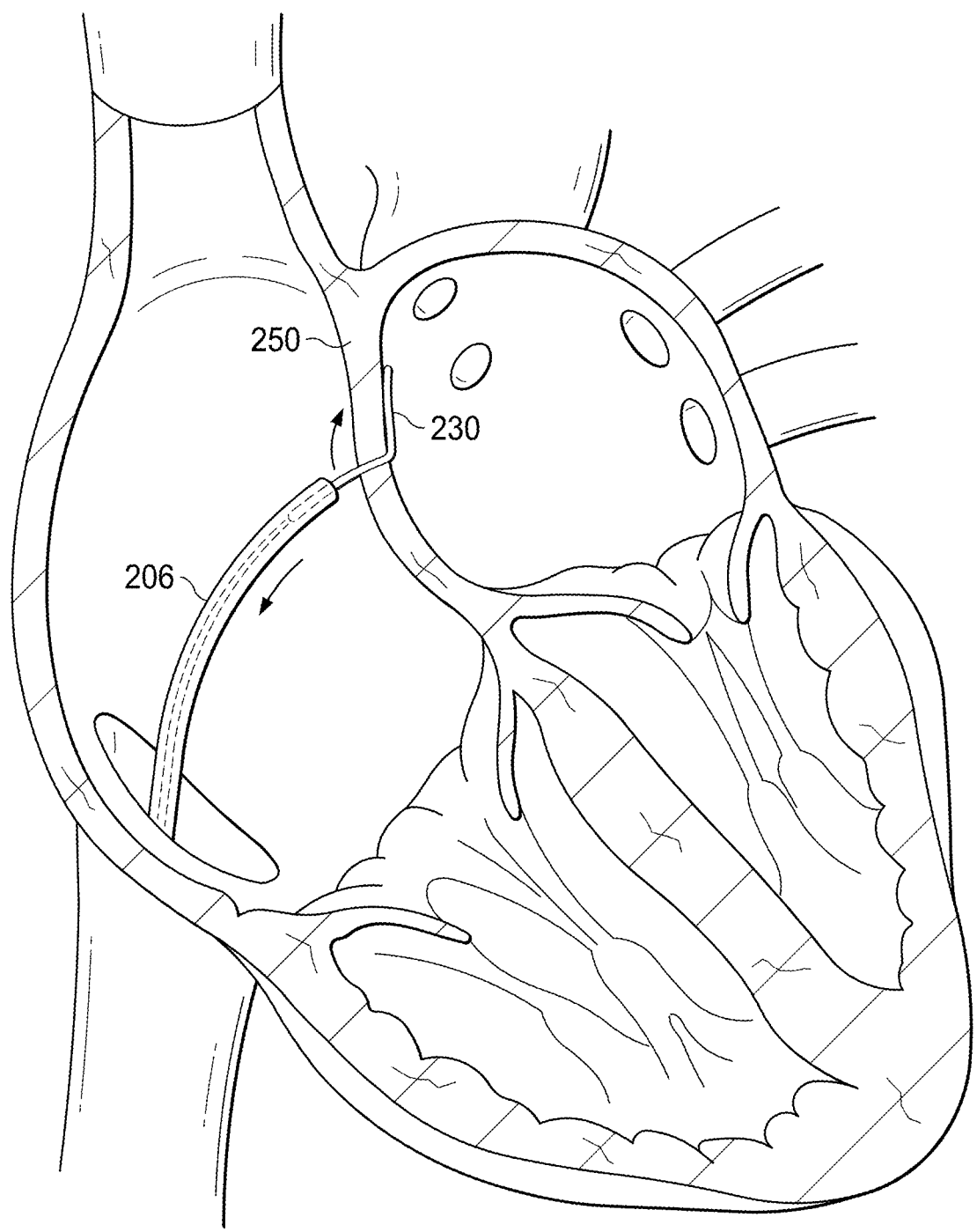

FIG. 2F depicts the further retraction of the anchor delivery sheath 206 and exposure of the septal electrode 230 against the atrial septum. The septal electrode 230 may comprise gold, nitinol or other suitable (e.g., inert and biocompatible) metal to transmit electricity to the heart. The septal electrode 230 maintains pressure against the atrial septum when deployed. The septal electrode 230 will maintain slight pressure on the septum to prevent movement of the device after it is deployed. As will be seen in the examples of FIG. 3A, the septal electrode 230 permits electrical current to flow to the septum 250 (and beyond) from an electronics enclosure.

Figure 2G:
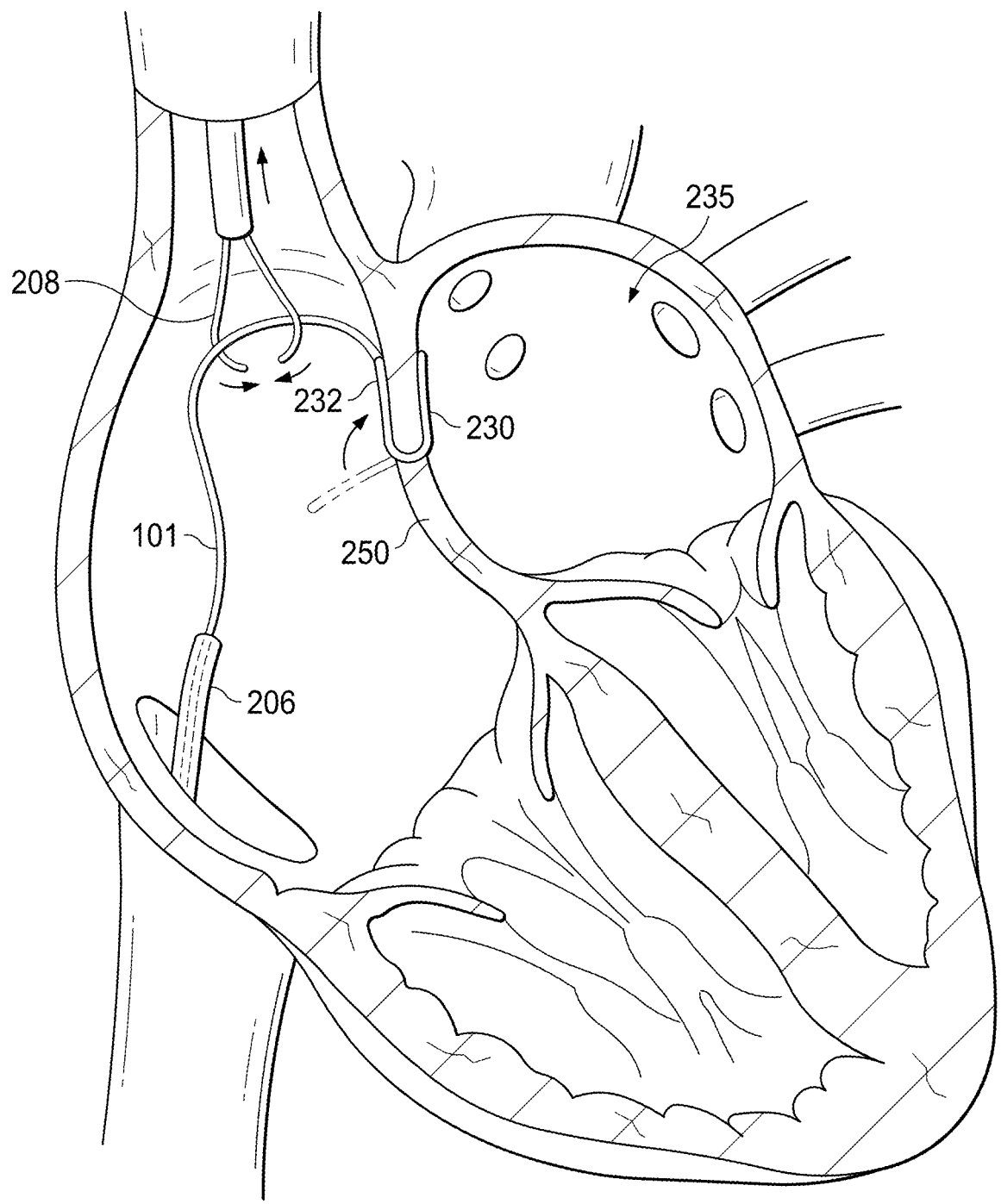

FIG. 2G depicts the septal electrode 230 fully deployed against the atrial septum 250. A snare device 208 is then depicted which allows the distal region of the lead to be moved from its insertion site (e.g., the groin) to the subclavian area or some other chest position at which the electronics enclosure is located. A portion 232 of the septal electrode 230 in the right atrium on the opposite side of the septum 250 from the portion of the septal electrode 230 in the left atrium is bent upward as shown using the snare device 208 thereby forming a U-shaped structure as shown. Because of the mechanical properties of the device (e.g., the memory shape structure), the wires will hug the endocardial surface.

Figure 2H:
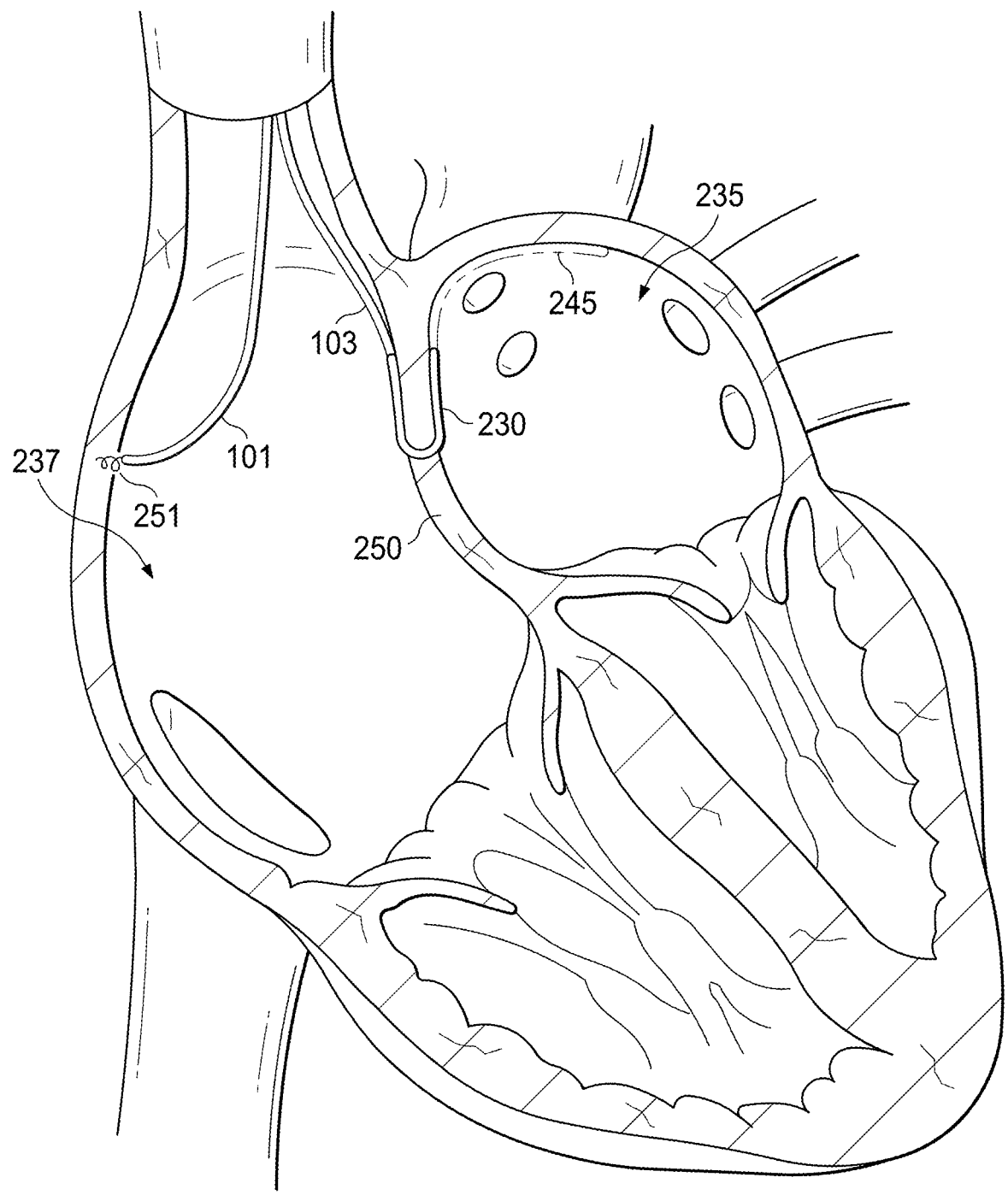

In other examples, the portion of the electrode pressed against the atrial septum in the left atrium may be longer than that shown in FIG. 2G or there be an additional array attached to the lead anchor 207 to increase the surface area along the atrial septum 250 and/or left atrium 235. For example, FIG. 2H depicts an extension 245 of the septal electrode 230 to increase the surface area for defibrillation of the left atria 235. Again, a shape memory metal (e.g., Nitinol) covering will hold the extensions tight against the atrial wall. Electrode 230 may be coated with a material such as gold to increase its conductivity. The curved wire can be made of nitinol or other shape memory material that can be straightened for implantation through a sheath into the patient—the curve shape can form inside the patient. The memory metal wire assembly can have the memory metal or similar material on the outside covering of the wire, as a part of the wire with insulation covering the wire or with any combination of a steroid, heparin coating or drug eluting coating. The device sits relatively flat against atrial wall (i.e., in continuous contact with the atrial wall such as the atrial septal wall) and eventually becomes strongly embedded in the cardiac tissue. This low profile discourages thrombus formation. The device has excellent electrical contact. The restraining device is held passively against the atrial septum. The restraining device easily attaching to the atrial septum with a low profile provides a safe route for deployment.

This figure also depicts both leads 101 and 103 exiting in the left subclavian area or other site on the chest An electrode 251 is shown at the distal end of lead 101 and anchored into the right atrium 237.

Figure 3A:
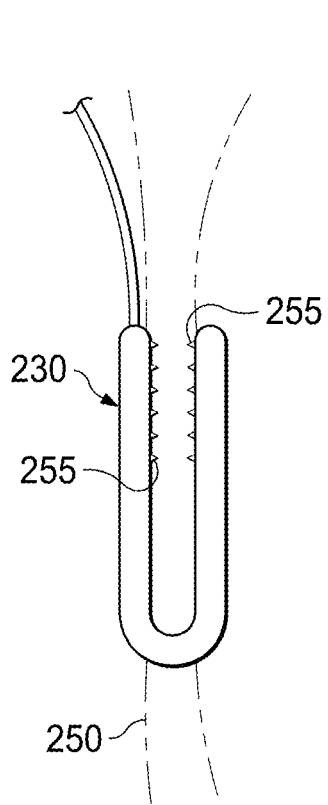
FIG. 3A shows a dose-up view of one example of the septal electrode which includes protrusions to help hold the septal electrode in place against the septum.
Figure 3B:
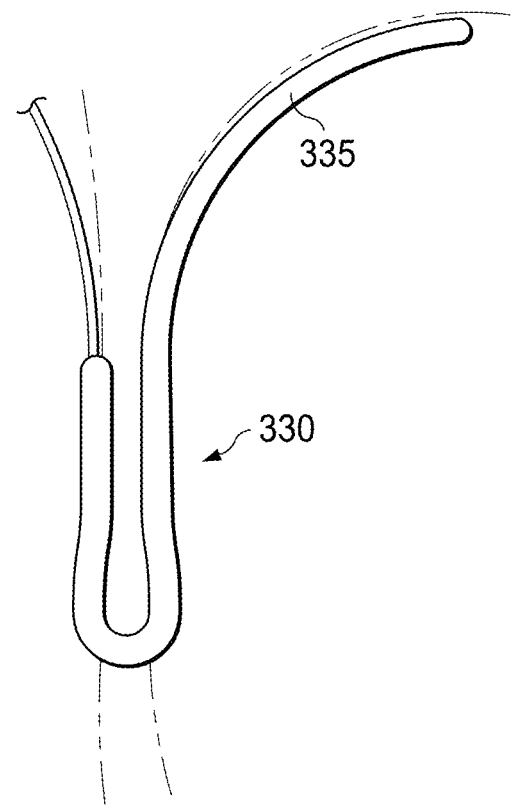
FIG. 3B shows another example of a septal electrode with extension further into the left atrium, again with the wires and electrode flush against the endocardium.
Figure 3C:
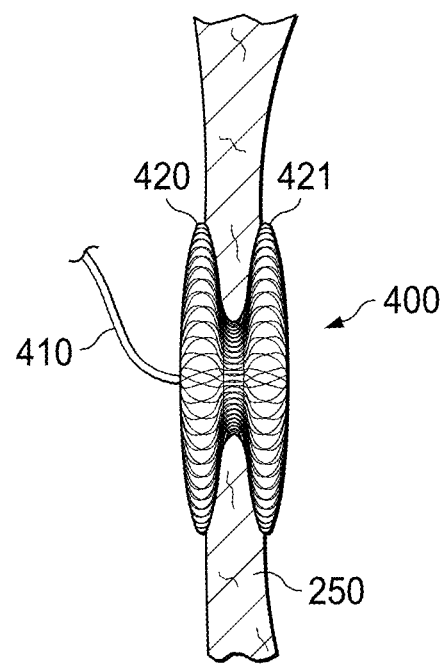
FIG. 3C shows yet another example of a septal electrode with deployable wings held in place by the device against the atrial wall.

FIGS. 3A-3C depict examples of devices that specifically allow for atrial defibrillation with two electrodes. One of the electrodes is placed in the right atrium (e.g., electrode 251 shown in FIG. 2H), but other locations are possible as well such as the right ventricle, left ventricle, or coronary sinus. The other electrode comprises the septal electrode 230 that sits along the atrial septum. FIG. 3A depicts a septal electrode 230 hugging both sides of the atrial septum 250. Protrusions 255 (e.g., teeth) extend towards and slightly into the septum 250 and allow secure positioning along the septal wall to help anchor the septal electrode 230 in place on opposite sides of the septum 250.

FIG. 3B is similar to FIG. 2H and depicts a septal electrode 330 hugging the atrial septum with a left atrial (could also be right) extension 335 for additional surface area (compared to septal electrode 230 in FIG. 3A) for defibrillation. Protrusions 255 may be included in this embodiment as well to help hold septal electrode 330 and its extension 335 in place.

FIG. 3C depicts an alternate septal electrode 400 which covers both sides of the atrial septum 250. Septal electrode 400 comprises a plug having an electrode array. The plug can have electrode properties, or the plug may incorporate electrode(s) with sufficient conductivity, such as gold plating. The extra electrode(s) can be weaved into the plug, or can be a circular electrode on one or both sides of the device, or can be more than one electrode in circles about the circumference or radius or in between the plug. The extra electrode is attached to a wire 410 which exits the heart in the same manner as the device in FIGS. 3A and 3B. Opposing wings 420 and 430 can be deployed (e.g., fan out) to anchor the device against the septum 250 as shown.

Figure 4A:
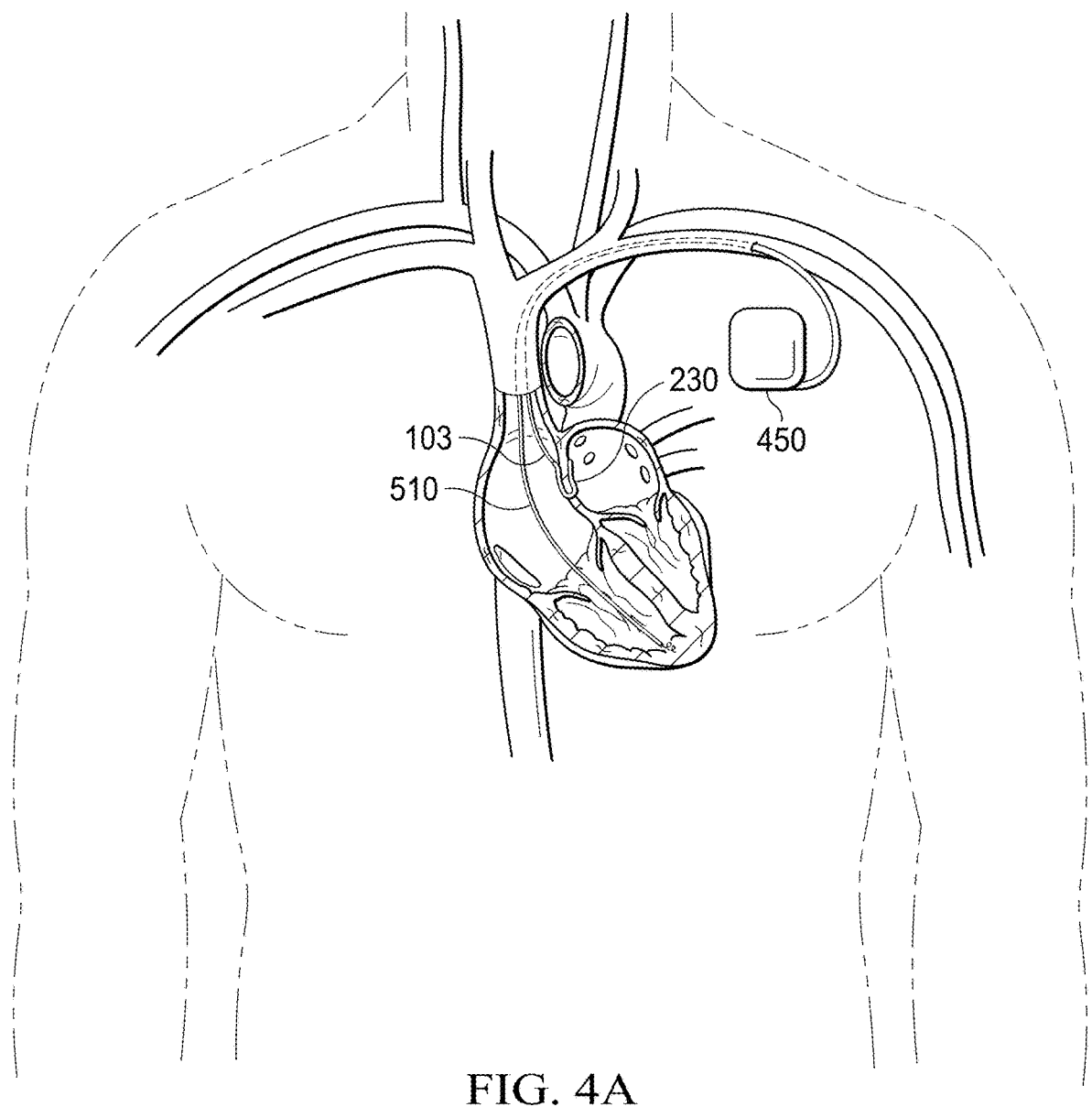
FIG. 4A shows an example of an implantable medical device with a septal electrode on one lead and another electrode on a second lead into the right ventricle.
Figure 4B:
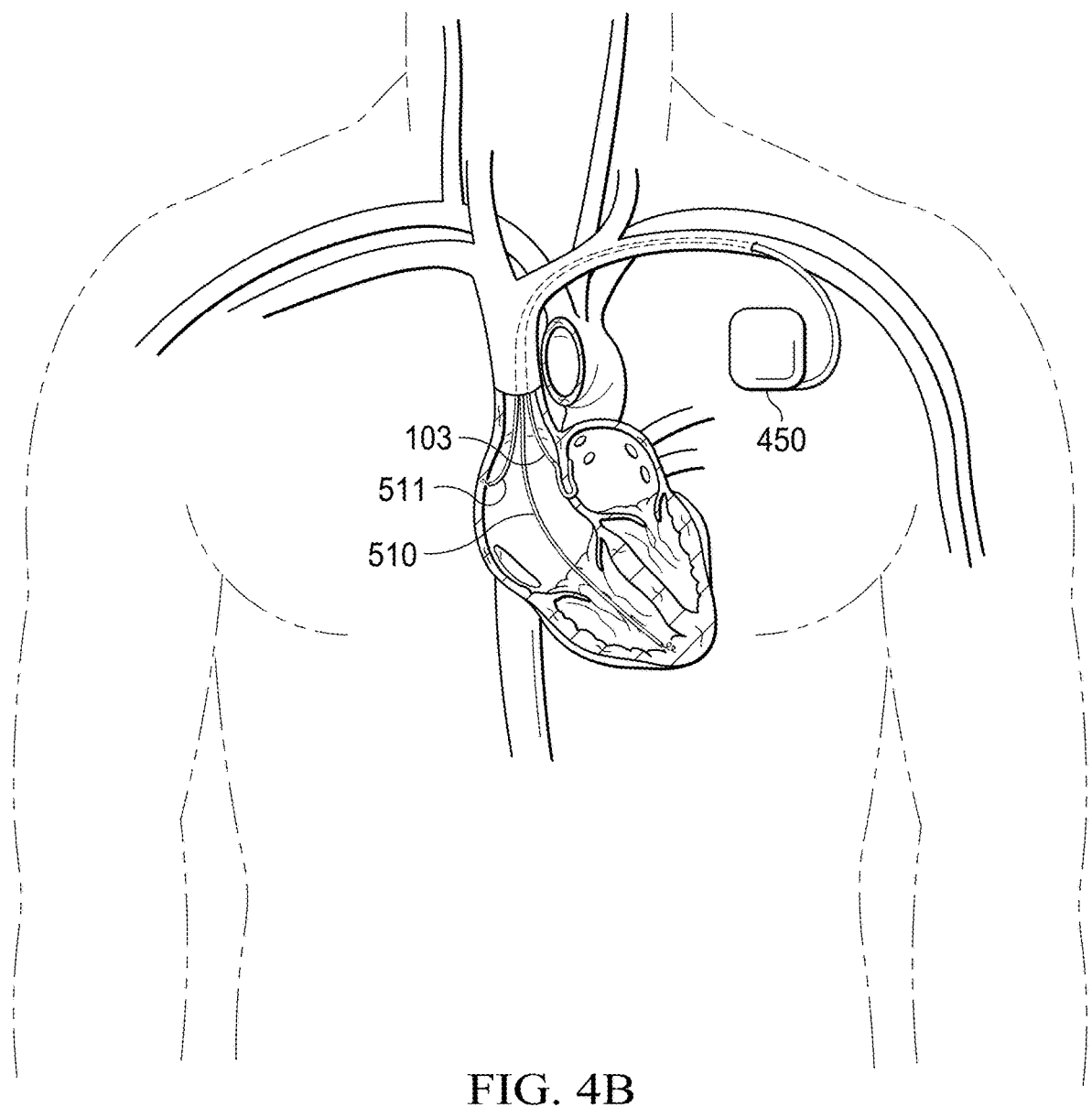
FIG. 4B shows an example of an implantable medical device with a septal electrode on one lead, and two additional leads anchored into the right atrium and right ventricle.

FIG. 4A shows an atrial defibrillator (or pacemaker, sensor, or recording device) implanted in a person with the septal electrode 230 of lead 103 connected to a battery-powered electronics enclosure 450 (similar to electronics enclosure 110 described above) and attached to the atrial septum and another lead 510 provided into and anchored to the right ventricle. The electronics enclosure comprises a sealed enclosure, a battery contained therein, and a circuit to generate electrical stimulation signals to be provided to the electrodes at the distal ends of the leads. FIG. 4B shows the atrial defibrillator implanted in a person with the septal electrode 230 of lead 103 attached to the atrial septum, a second lead 510 provided into and anchored to the right ventricle, and a third lead 511 anchored into the right atrium.

Figure 5:
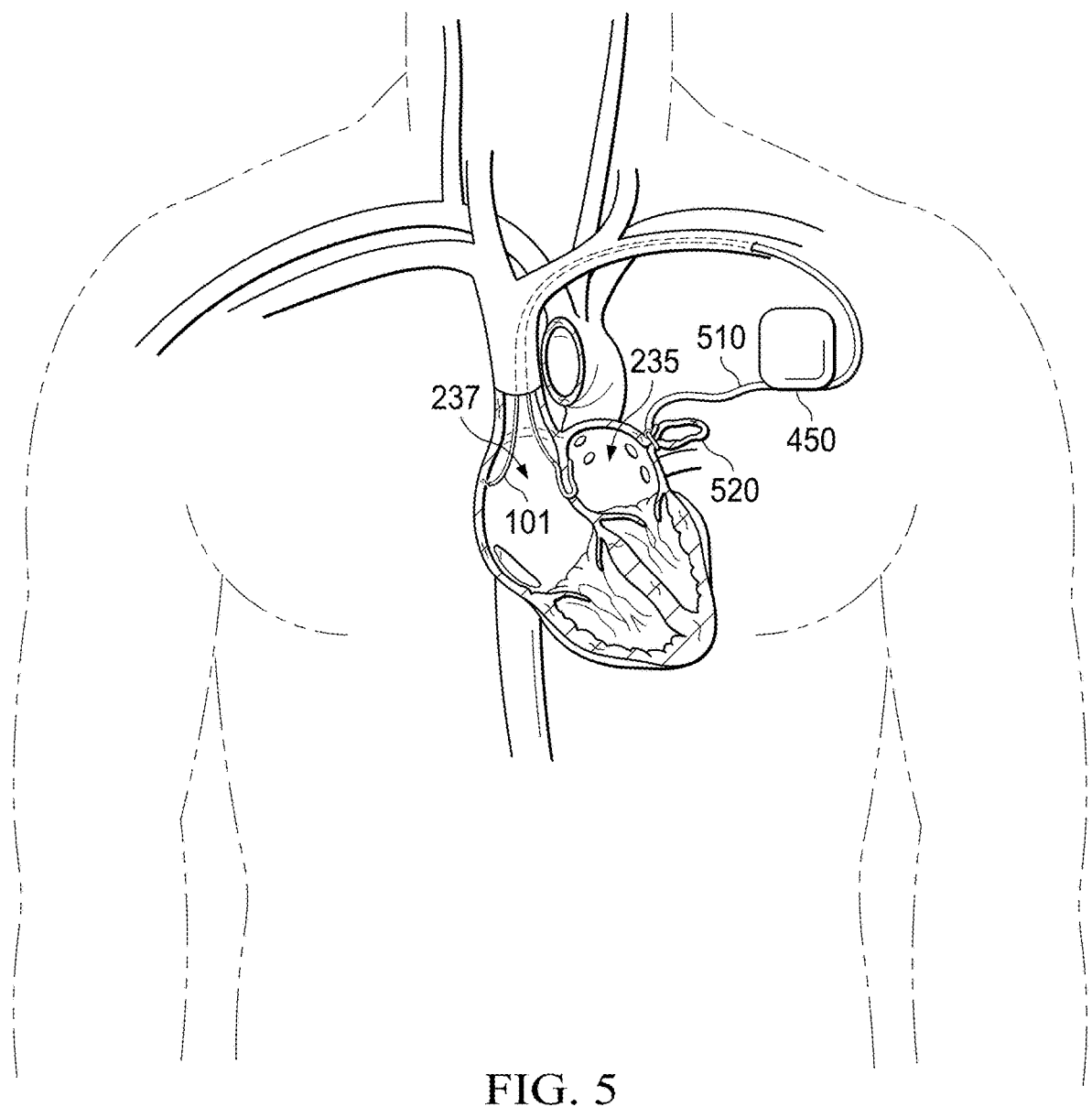
FIG. 5 illustrates another embodiment in which an electrode is part of an atrial appendage closure device in which the closure device is external to the atrial appendage, which keeps the wire of the device tight against the atrial wall.

FIGS. 5-7 illustrate an embodiment in which an atrial electrode is included in a device that occludes an orifice of the atrial appendage from outside the heart. FIG. 5 depicts an arrangement of the leads of a defibrillator with one atrial lead 101 placed in the right atrium 237. A second atrial lead 510 is placed in or about the atrial appendage 520 of the left atrium 235 and is attached to an atrial appendage closure device that is used to dose the orifice between the left atrium 235 and the atrial appendage 520. The leads 101 And 510 and their electrodes allow for specific atrial defibrillation of the atria, with a very small amount of energy (approximately 1-10 joules). The device extensions contain memory shaped metal or another composition, such as plastic, which holds the extensions tight against outside of the left atrium. FIG. 5 also shows the pulse generator 450 which comprises a sealed enclosure containing a battery and a circuit to generate the stimulation energy to electrodes at the distal end of the lead(s) 101 and 510.

Figure 6A:
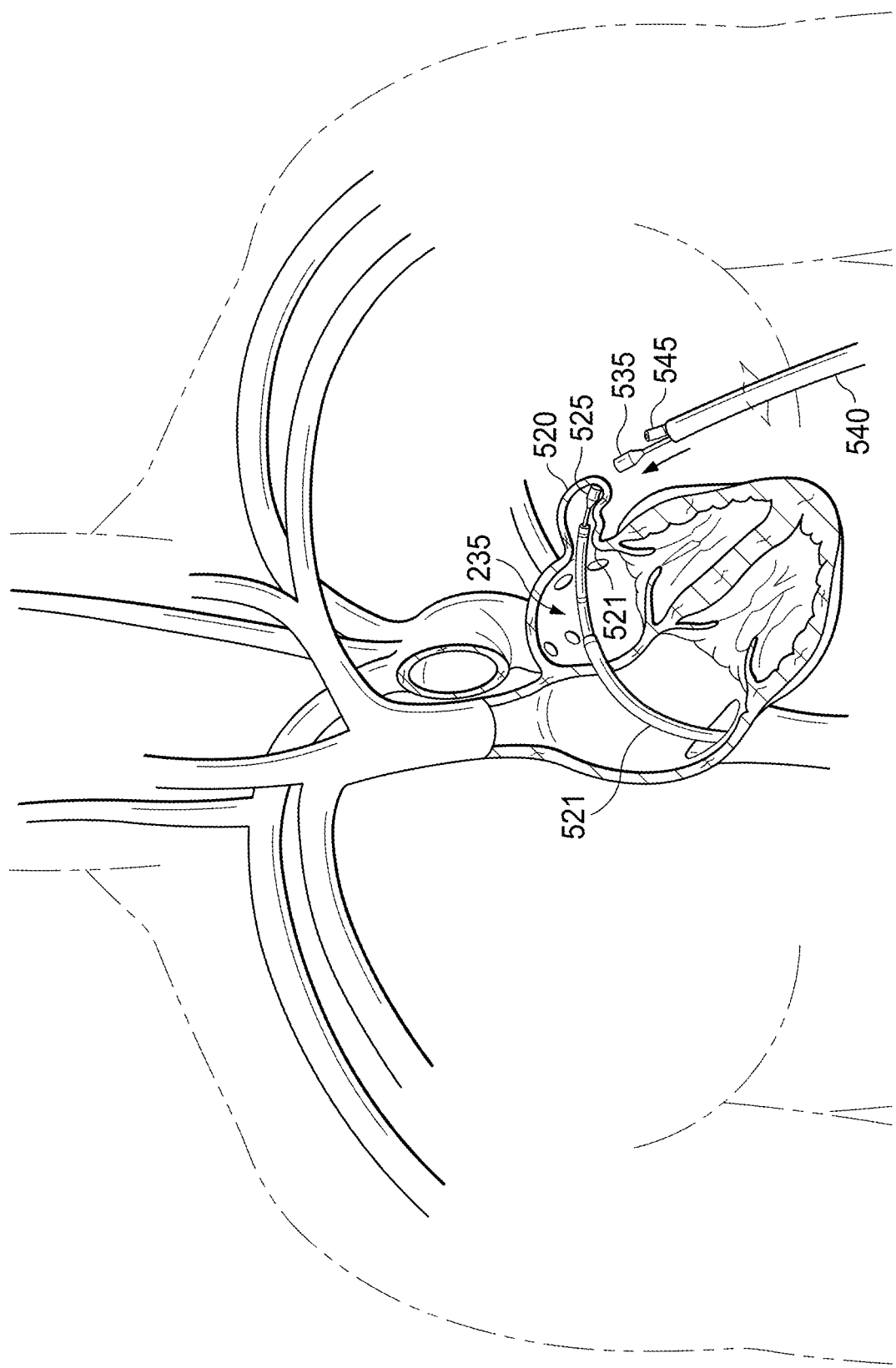

FIG. 6A shows a portion of the procedure to implant an atrial appendage closure device around the atrial appendage 520. Installation of the atrial appendage closure device includes a magnet 525 positioned via a sheath 521 inside the atrial appendage 520. A second magnet 535 is brought near magnet 525 from outside the heart via a sheath 540 inserted through a small incision in the patient's chest The orifice 521 is shown between the left atrium 235 and the atrial appendage 520. Once the magnet 535 is brought dose enough to magnet 525, the magnetic attraction causes the two magnets into contact with the wall of the atrial appendage 520 sandwiched therebetween. The magnets stabilize the atrial appendage 520. FIG. 6A also shows the distal end of a sheath 545 containing a lariat (discussed below).

Figure 6B:
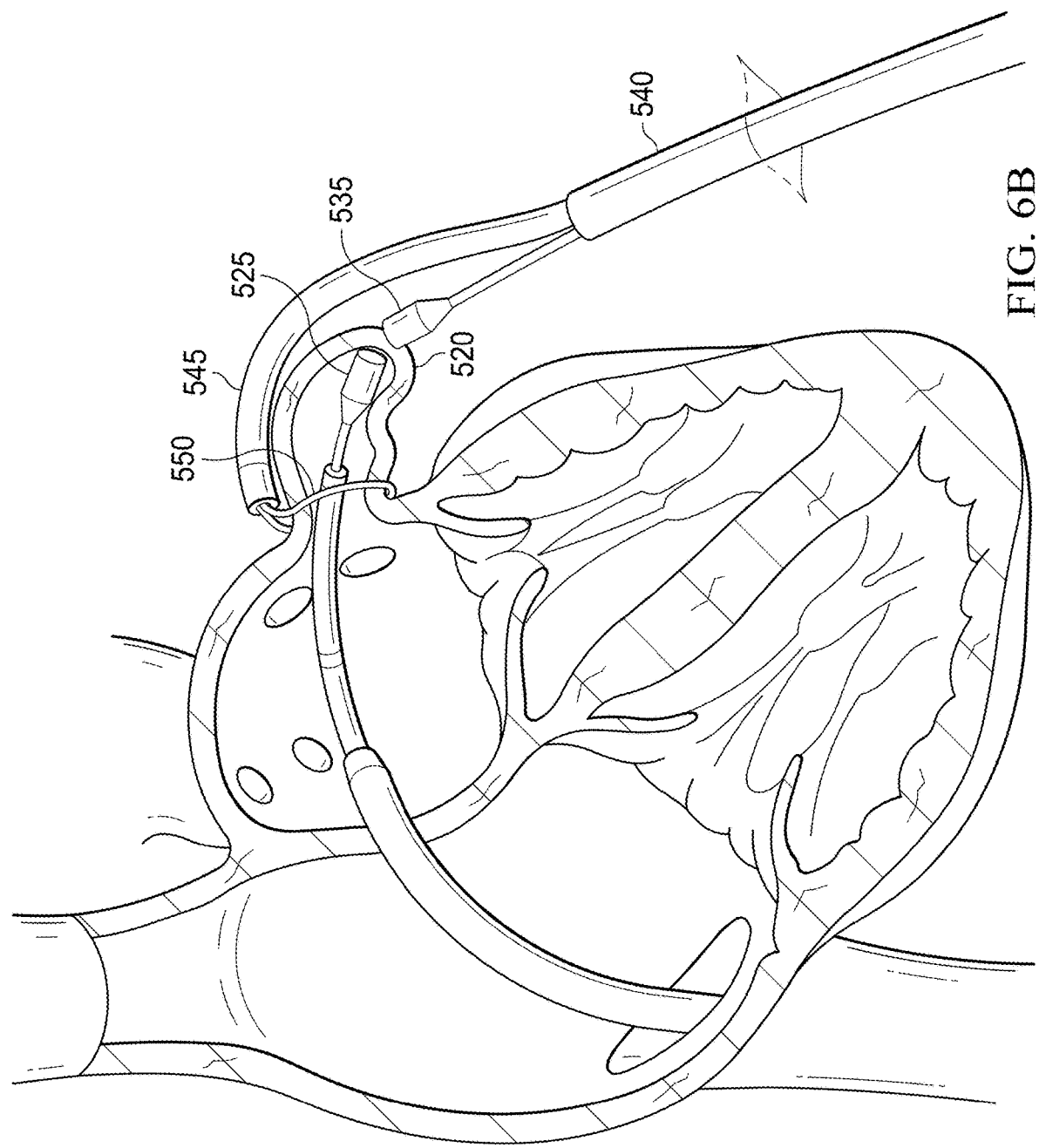

FIG. 6B depicts the deployment of a lariat 550 around the base of the atrial appendage 520. The lariat 550 may be made of suture material or wire. FIG. 6C depicts a lead extension with electrodes 560 and 565 attached to the lariat 550. The electrodes can be placed on the lariat device before insertion into the body. The electrode array may vary depending on which configuration provides the optimal delivery of joules at the lowest resistance. There can be one or more electrodes fixed to the lariat. The electrodes may be longer and unfurl against the outside of the LA upon deployment. The covering or composition of the extensions contain memory shaped metal or other material that ensures the extensions remain in contact with the left atrium, or other epicardial surfaces. The specific length and number of electrodes and whether they unfurl depends on the energy needed to deliver the appropriate energy for defibrillation and the acceptable resistance generated. FIG. 6D shows the lariat 550 in place and cinched around the base of the of the atrial appendage 520 thereby closing off the orifice from the left atrium 525 into the atrial appendage. FIG. 6D also shows the electrode 560 positioned on the lariat 550 and thus just outside the left atrium.

FIG. 7 depicts the electrode 560 separate from the lariat 550. In this example, the electrode 550 is a coiled spring electrode. The electrode may unfurl and be present on the outside of the LAA base and or LA. There can be more than one electrode. The configuration can be a star or circle or other shape. However, the configuration of the electrode 560 may be other than that shown in FIG. 7 in other embodiments. In other examples, the portion of the electrode pressed against the left atrial tissue may be longer than that shown in FIG. 7 or there may be one or more additional electrodes on the lariat 550 to increase the surface area along the left atrium. The configuration of the electrode array may vary somewhat also to accommodate the size of the atrial appendage closure device.

FIGS. 8A-8D illustrate the closure of the orifice between the left atrium 235 and the atrial appendage 520 from inside the heart using a plug 810 (also referred to as a left atrial appendage occluder). The plug 810 is fitted with one or more electrodes connected to a pulse generator (e.g. pulse generator 450) and used for defibrillation. One or more other electrodes are positioned in the right atrium, right ventricle, left ventricle, coronary sinus, or intra-atrial septum. The plug 810 is deployed through a sheath 805.

Figure 8A:
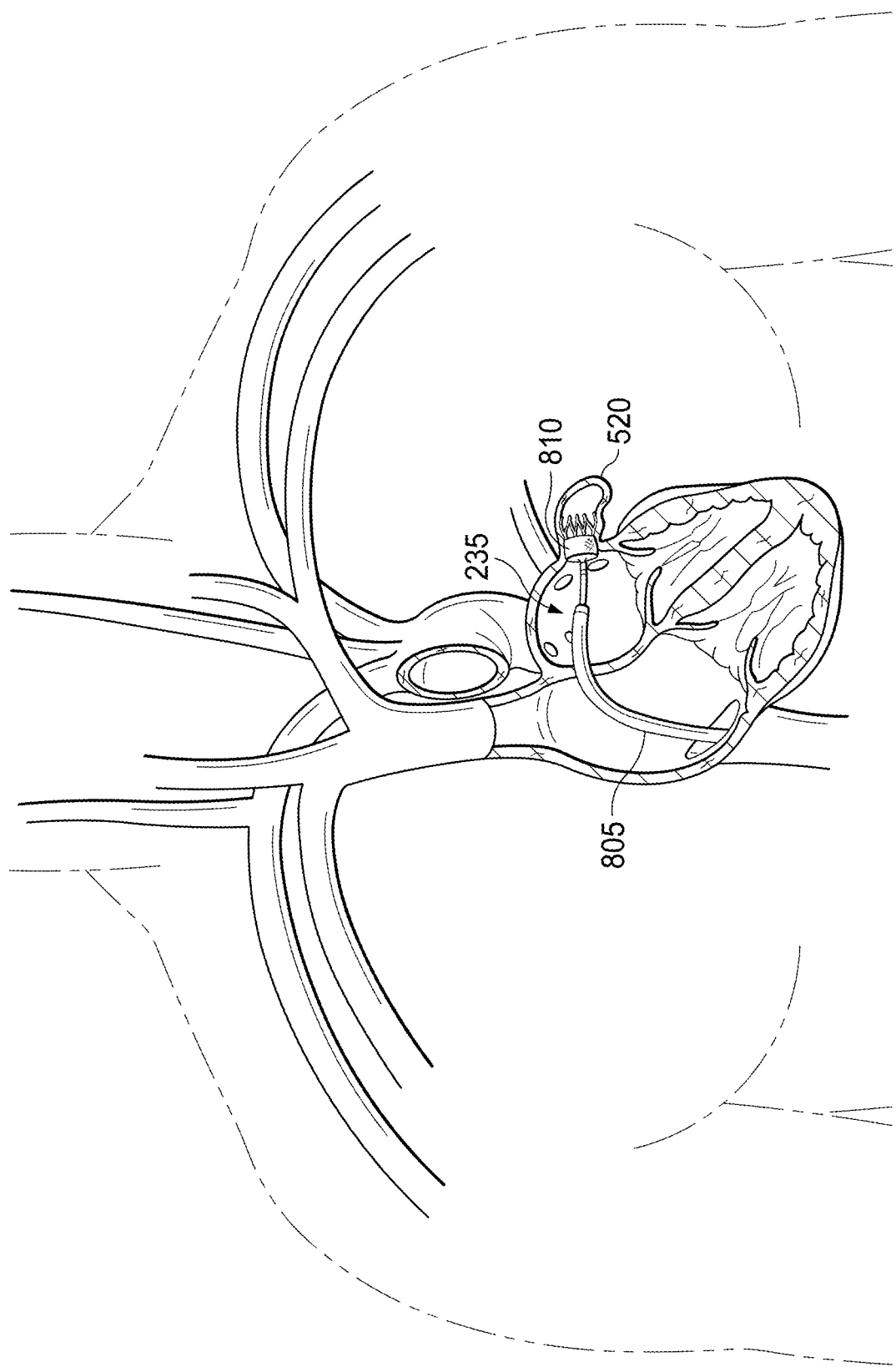
FIGS. 8A-8D illustrate another embodiment in which an electrode is part of an atrial appendage closure device in which the closure device is internal to the atrial appendage.
Figure 8B:
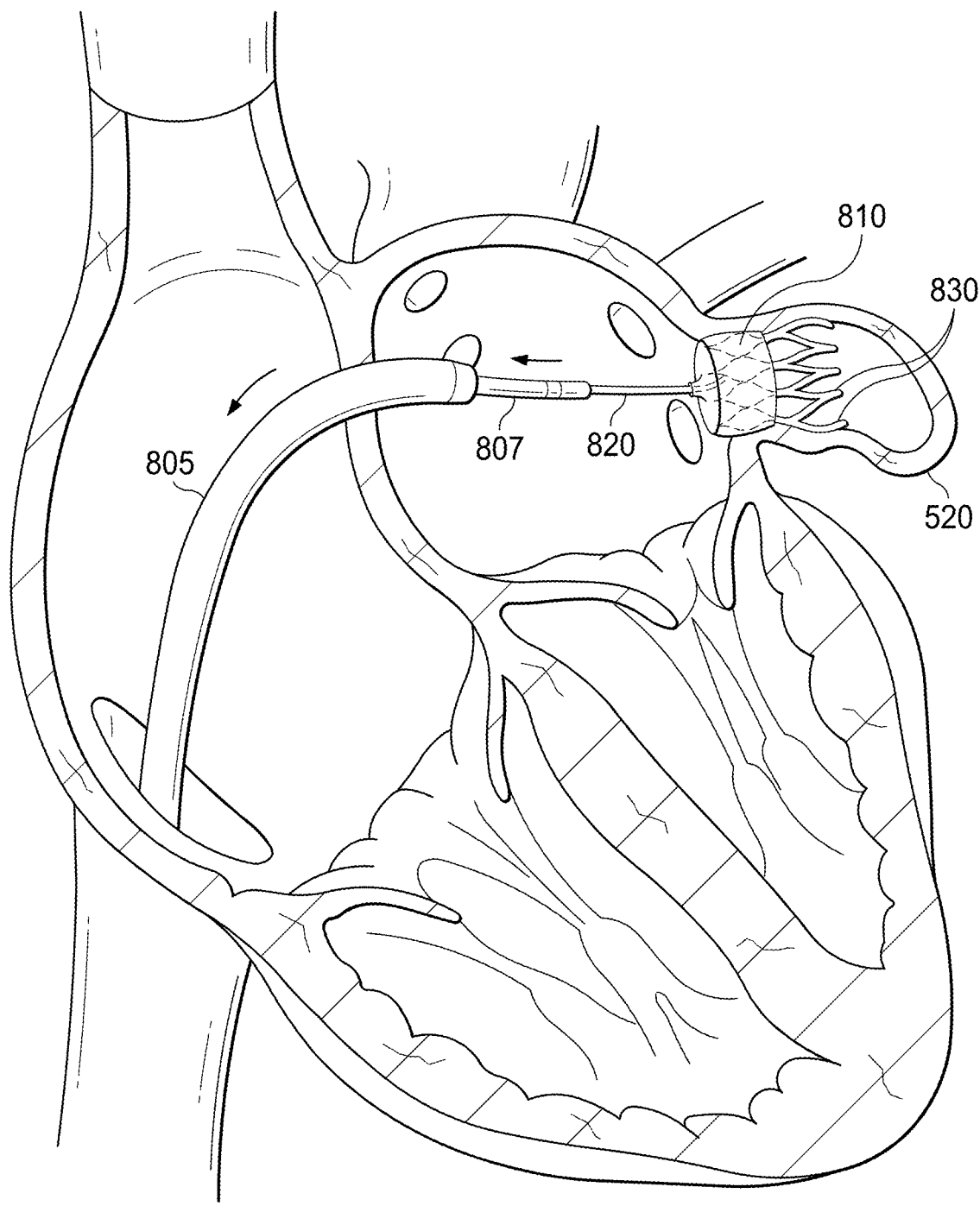

FIG. 8B shows the retraction of the sheath 805 and a plug deployment member 807. A lead 820 is shown inside the plug deployment member 807. The lead 820 is exposed when the sheath 805 and plug deployment member 807 are retracted. Electrodes 830 are shown on the lead 820 inside the atrial appendage 520. The device keeps the wires snugly against the inside heart walls, which keep the wires out of the flow of blood. In this position, the wires become embedded in the atrial wall.

Figure 8C:
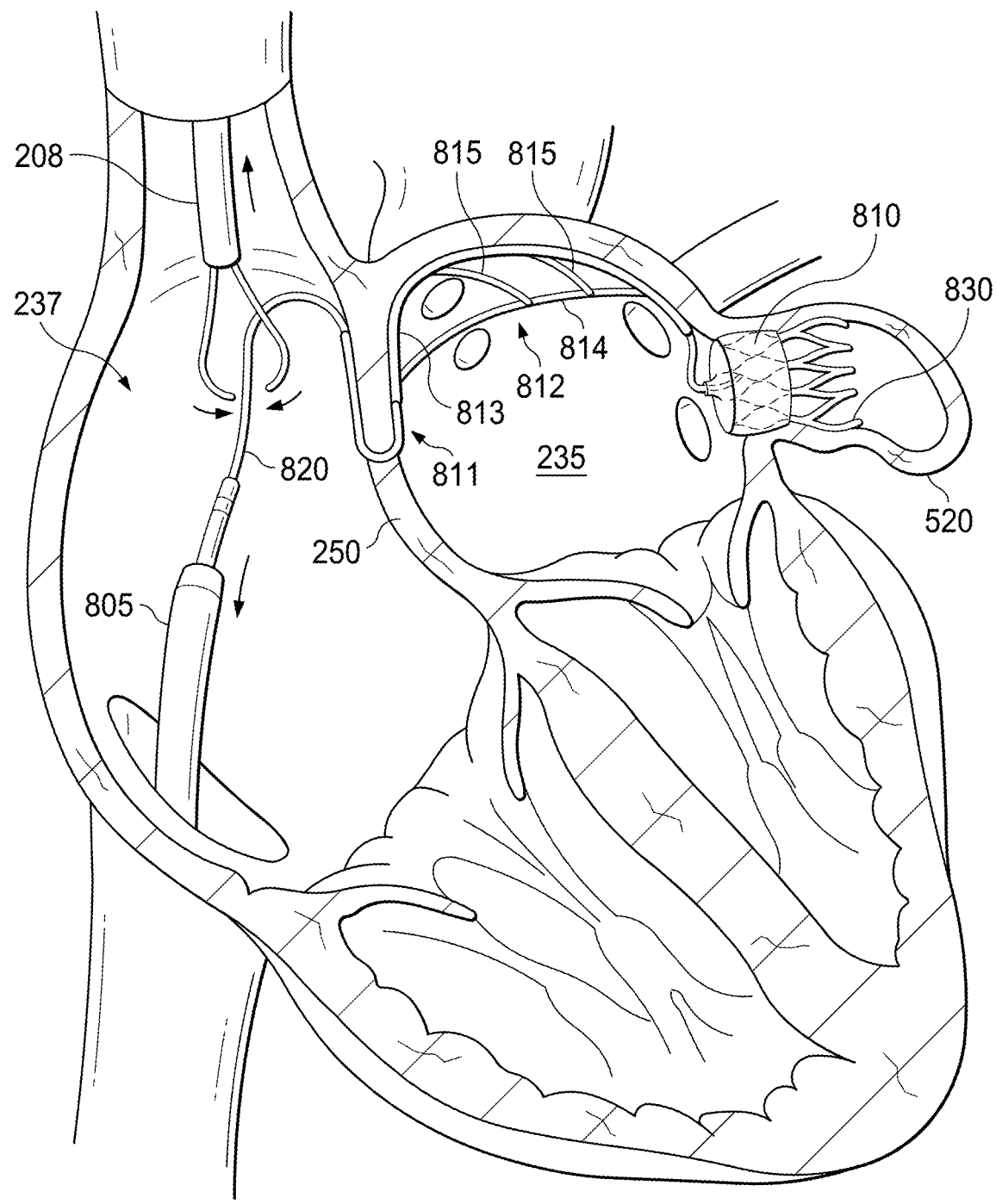

In FIG. 8C, the lead 820 from the left atrial closure device (plug 810) extends from the device and upon retraction of the sheath 805 and plug deployment member 807 brings the attached lead 820 into the right atrium 237. In the right atrium 237, the lead is then grasped or directed with a snare device 208 to be delivered into the left or right subclavian vein or other vein for connection to a pulse generator 450 that would be placed subcutaneously as described above. FIG. 8C also shows a lattice 812 coupled to a U-shaped clip 811 that is coupled to the septum 250. The lattice includes, for example, a first wire 812 and a second wire 813, both coupled to the U-shaped clip 811 and configured to be restrained against the endocardium of the left atrium 235. More than two wires can be included as desired. The wires 812 and 813 are interconnected and spaced apart by one or more interconnecting wires 815, also which are restrained against the wall of the left atrium. The U-shaped clip 811 and wires 813, 814, and 815 may be formed from any suitable type of shape memory metal, such as Nitinol.

Figure 8D:
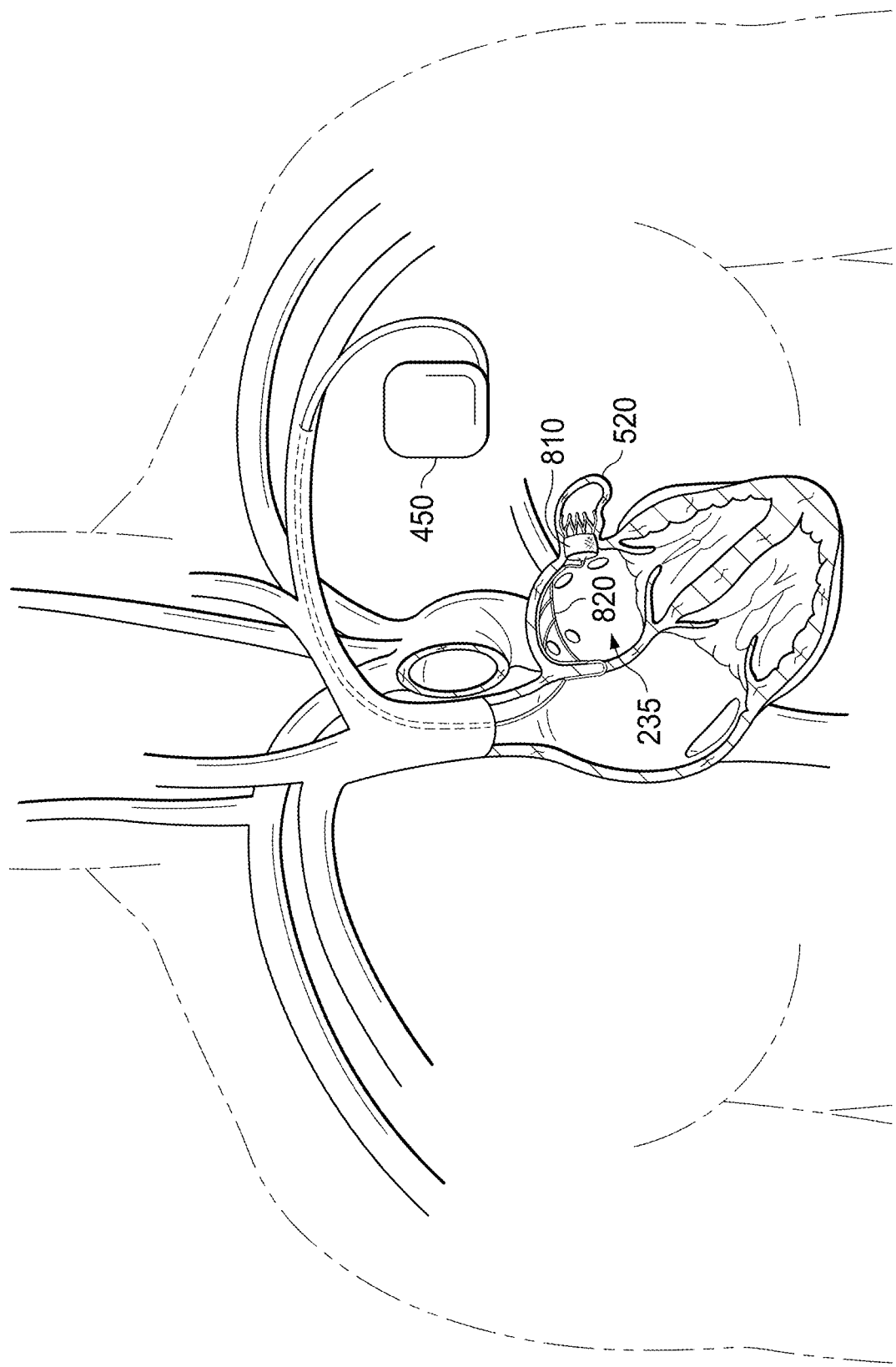

FIG. 8D shows the final configuration of plug 810 closing off the atrial appendage 520 with the left atrial lead 820 extending from the left atrial closure device (plug 810), extending along and hugging the interior wall of the left atrium 235. The wire then traverses the atrial septum to the right atrium. The lead 820 then extends through the superior vena cava (alternatively, the inferior vena cava) to a more peripheral vein that would allow access to the pulse generator 450 (which may be configured to perform defibrillation and/or pacing). A right atrial (as in FIG. 1, lead 101) may also be present and connected to the pulse generator 450. Such additional lead could also be a lead positioned in, for example, the right ventricle, left ventricle, or coronary sinus lead.

In the example of FIGS. 8C and 8D, the active electrode (providing stimulation or sensing capability) can be provided on the lattice 812 (e.g., wire 814), in or on the plug 810, or on both the lattice and the plug. In one embodiment, the electrode is on one of wires 813 or 814 of the lattice 812, and the other wire 813, 814 of the lattice with its shape memory helps to force the electrode-carrying wire into continuous contact with the atrial wall. In one embodiment, the lattice 812 is present but not the plug 810. Further, the U-shaped clip 811 may or may not have an electrode. In one example, the clip 811 functions as an anchor for another structure (e.g., the lattice 812, a pacing lead, etc.) and is not itself used for sensing or stimulation purposes.

Figure 9:
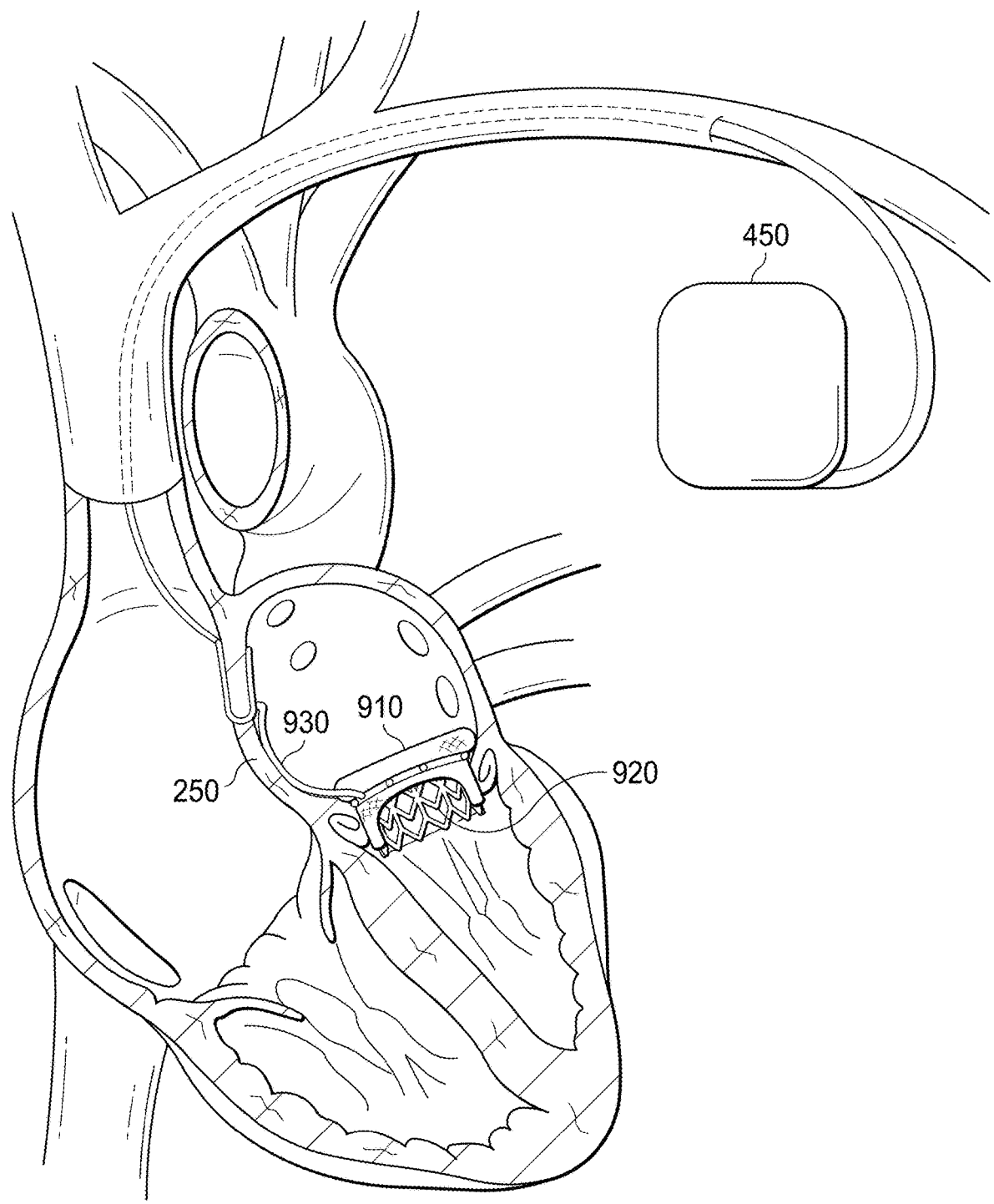
FIG. 9 shows an embodiment in which an electrode is part of a mitral valve device in which the wires are connected to the electrodes on the mitral annulus and hug the atrial septum, and connect to the electrode embedded in the septum.

In another embodiment, a left atrial lead can be incorporated a mitral valve replacement and/or mitral valve repair, either transseptal via a percutaneous approach or minimally invasive or open surgical approach. For example, an electrode array can be incorporated into mitral valve devices that touch or are near the left atrium. FIG. 9 shows a prosthetic mitral valve device 910 which is incorporated with one or more electrodes 920 forming an electrode array. The electrodes 920 are on the distal end of an atrial lead. The lead 930 would then be routed through the atrial septum 250 and connected to a pulse generator 450 as described above. The orifice of the mitral valve, where most mitral valve devices (such as mitral valve device 910) are positioned, is a suitable site for bi-atrial defibrillation with the device described herein. One configuration of the electrode array would be a conductive thin wire woven or otherwise attached to the valve device 910 as it sits around the mitral orifice. The mitral valve device 910 or devices may accommodate the electrode array and lead 930. Lead 930 can extend and overlap with the septal restraining device. The septal restraining device then connects to an insulated wire which connects to a pacemaker and/or defibrillator or transducer. The mechanical properties of the device hold the wires and extensions against the atrial wall, where tissue ingrowth will occur, as it does with the implanted mitral valve. The lead 930 can also allow attachment to another grasping device (e.g., snare device 208) to bring the wire to the appropriate site near the defibrillator/pacemaker pocket.

Some embodiments are directed to a support structure for a pacemaker lead. The support structure is coupled to the pacemaker lead and is configured to restrain a portion of the pacemaker lead against a person's atrial wall. Examples of the support structure are described herein and include, for example, a U-shaped clip, a lattice, etc. the support structure may comprise a shape memory material (e.g., Nitinol).

Using the structures described herein, a method for implanting a lead in the left side of a heart can comprise introducing the lead into a blood vessel, advancing the lead into a left atrium, fixing a distal region of the lead in position flush against the atrial septum with anchor elements on both sides of the atrial septum, and affixing an electrode on the lead in contact with the endocardium of the heart. Further, advancing the lead into the left atrium may include advancing the electrode beyond the septum and into continuous contact with the atrial wall. A lattice may be positioned in the left atrium to maintain the distal region of the lead in contact with the atrial wall.

Modifications are possible in the described embodiments, and other embodiments are possible, within the scope of the claims.

The invention claimed is:

1. An implantable medical device, comprising:
a cardiac lead having a distal region and a proximal end, the proximal end of the cardiac lead adapted to be coupled to an electronics enclosure, the distal region of the cardiac lead having a structure configured to hold a portion of the distal region of the lead against a person's endocardium, the structure including a center portion disposed between side portions coaxially extending from respective ends of the center portion, the side portions configured to extend along opposite sides of an atrial septum while the center portion spans the atrial septum to secure the structure to the atrial septum;
wherein the distal region of the lead also has an electrode that extends away from the structure and an elongated portion of the electrode is configured to maintain contact with the person's endocardium.

2. The implantable medical device of claim 1, wherein the structure comprises a septal closure device.

3. The implantable medical device of claim 1, wherein the structure comprises a shape memory material.

4. The implantable medical device of claim 1, wherein the structure includes protrusions configured to mate to the endocardium.

5. The implantable medical device of claim 1, wherein the center portion and side portions of the structure form a U-shaped clip.

6. The implantable medical device of claim 5, wherein the electrode is on the U-shaped clip and extends from the side portions of the structure.

7. The implantable medical device of claim 1, wherein the distal region includes a wire extension coupled to the structure and configured to be restrained against the person's endocardium.

8. The implantable medical device of claim 7, wherein the electrode is on the wire extension.

9. The implantable medical device of claim 1, wherein the structure comprises a lattice.

10. The implantable medical device of claim 9, wherein the lattice is configured to restrain the distal region of the cardiac lead to the person's endocardium.

11. The implantable medical device of claim 9, wherein the electrode is on the lattice.

12. The implantable medical device of claim 9, further including a U-shaped clip configured to attach to a septum of the person, and wherein the lattice comprises:
a first wire coupled to the U-shaped clip and configured to be restrained against the person's endocardium;
a second wire also coupled to the U-shaped clip and configured to be restrained against the person's endocardium;
an interconnecting wire connected to the first and second wires to space apart the first and second while restrained against the person's endocardium.

13. The implantable medical device of claim 1, further including a mitral valve device, and the electrode is part of the mitral valve device.

14. The implantable medical device of claim 13, wherein:
the shape memory structure includes a U-shaped clip configured to be attached to the person's septum; and
the electrode is coupled to the U-shaped clip by way of a shape memory wire that is configured to be restrained against the person's endocardium between the mitral valve device and the U-shaped clip.

15. The implantable medical device of claim 1, wherein the electrode contains memory-shaped metal and is shaped to cause the elongated portion of the electrode to maintain contact along the person's endocardium.

16. The implantable medical device of claim 1, wherein the elongated portion of the electrode includes a proximal end at the structure and a distal end, and wherein the electrode being configured to maintain contact along the person's endocardium has a shape that causes the electrode between the proximal end and the distal end to extend along the person's endocardium.

17. The implantable medical device of claim 16, wherein the electrode between the proximal end and the distal end extends along the person's endocardium along the atrial septum and away from the atrial septum.

18. The implantable medical device of claim 16, wherein the electrode is in continuous contact along the person's endocardium along and away from the atrial septum from the proximal end to the distal end.

19. An implantable medical device, comprising:
a pacemaker lead having a distal end and a proximal end, the proximal end of the pacemaker lead adapted to be coupled to an electronics enclosure, the distal end of the pacemaker lead having an electrode; and
a support structure coupled to the pacemaker lead and configured to restrain an elongated portion of the pacemaker lead against a person's atrial wall and away from an atrial septum, the support structure including a center portion disposed between side portions coaxially extending from respective ends of the center portion, the side portions configured to extend along opposite sides of an atrial septum while the center portion spans the atrial septum to secure the structure to the atrial septum.

20. The implantable medical device of claim 19, wherein the support structure is a lattice.

21. The implantable medical device of claim 19, wherein the center portion and the side portions of the support structure define a U-shaped clip configured to be retained to the atrial septum.

22. The implantable medical device of claim 19, wherein the support structure comprises a shape memory material.

23. The implantable medical device of claim 22, wherein the electrode comprises a shape memory material.

24. The implantable medical device of claim 19, wherein the electrode comprises a shape memory material.

25. The implantable medical device of claim 1, wherein the electrode includes an elongated portion that defines a side surface and a tip, the elongated portion of the electrode configured to maintain the side surface in contact with at least a portion of the atrial septum and the person's endocardium.

26. The implantable medical device of claim 1, wherein the electrode defines an elongated portion and a tip, and wherein the electrode is configured to maintain contact with the person's endocardium when the side surface of the tip is parallel with and in contact with the person's endocardium.

27. The implantable medical device of claim 1, wherein the center portion of the structure is an arc.

28. The implantable medical device of claim 27, wherein the arc is 180 degrees such that the ends of the arc are parallel with one another to cause the side portions of the structure to be in parallel with one another.

29. The implantable medical device of claim 1, wherein the side portions are configured to directly attach to opposite sides of the atrial septum.

30. The implantable medical device of claim 29, wherein the side portions are configured to be parallel with one another when directly attached to opposite sides of the atrial septum.

\* \* \* \* \*